United States Patent
Yuan

(10) Patent No.: US 8,772,312 B2
(45) Date of Patent: Jul. 8, 2014

(54) HETEROCYCLIC COMPOUNDS AS CRTH2 RECEPTOR ANTAGONISTS

(75) Inventor: Wei W. Yuan, Fishers, IN (US)

(73) Assignees: CSPC Zhongqi Pharmaceutical Technology (Shijiazhuang) Co., Ltd., Hebei (CN); Centaurus Biopharma Co., Ltd., Beijing (CN)

(*) Notice: Subject to any disclaimer, the term of this patent is extended or adjusted under 35 U.S.C. 154(b) by 164 days.

(21) Appl. No.: 12/681,356

(22) PCT Filed: Oct. 9, 2008

(86) PCT No.: PCT/US2008/079303
§ 371 (c)(1),
(2), (4) Date: Apr. 1, 2010

(87) PCT Pub. No.: WO2009/049021
PCT Pub. Date: Apr. 16, 2009

(65) Prior Publication Data
US 2010/0222270 A1    Sep. 2, 2010

Related U.S. Application Data

(60) Provisional application No. 60/998,298, filed on Oct. 10, 2007.

(51) Int. Cl.
| | | |
|---|---|---|
| C07D 471/06 | (2006.01) | |
| A61K 31/437 | (2006.01) | |
| C07D 471/14 | (2006.01) | |

(52) U.S. Cl.
CPC .................................... *C07D 471/14* (2013.01)
USPC ........................................... 514/292; 546/82

(58) Field of Classification Search
USPC ............................................ 546/82; 514/292
See application file for complete search history.

(56) References Cited

U.S. PATENT DOCUMENTS

| | | | |
|---|---|---|---|
| 7,144,913 B2 | 12/2006 | Wang et al. | |
| 7,618,979 B2 * | 11/2009 | Leblanc et al. | 514/290 |
| 7,696,222 B2 * | 4/2010 | Wang | 514/294 |
| 2005/0272756 A1 | 12/2005 | Leblanc et al. | |
| 2007/0191416 A1 | 8/2007 | Fecher et al. | |

FOREIGN PATENT DOCUMENTS

| | | | |
|---|---|---|---|
| WO | 2007019675 | * | 2/2007 |
| WO | WO 2009/140642 A2 | | 11/2009 |

OTHER PUBLICATIONS

Patani et al Bioisoterism, 1996.*
International Search Report for PCT/US2008/079303.
Supplementary European Search Report mailed Sep. 14, 2011 in European Application No. 08838211.

* cited by examiner

*Primary Examiner* — Rita Desai
(74) *Attorney, Agent, or Firm* — The Marbury Law Group, PLLC

(57) ABSTRACT

This application relates to a compound of Formula ! (or a pharmaceutically acceptable salt thereof) as defined herein, pharmaceutical compositions thereof, and its use as an antagonist of receptor CRTH2, as well as a process for its preparation and intermediates therefor.

15 Claims, No Drawings

HETEROCYCLIC COMPOUNDS AS CRTH2 RECEPTOR ANTAGONISTS

BACKGROUND OF THE INVENTION

Prostanglandin $D_2$ ($PGD_2$) is a cyclooxygenase metabolite of arachidonic acid. It is released from mast and TH2 cells in response to an immunological challenge, and has been implicated in playing a role in different physiological events such as sleep and allergic responses.

Receptors for $PGD_2$ include the "DP" receptor, the chemoattractant receptor-homologous molecule expressed on TH2 cells ("CRTH2"), and the "FP" receptor. These receptors are G-protein coupled receptors activated by $PGD_2$. The CRTH2 receptor and its expression on different cells including human T-helper cells, basophils, and eosinophils are described in Abe, et al., *Gene* 227:71-77, 1999, Nagata, et al., *FEBS Letters* 459:195-199, 1999, and Nagata, et al., *The Journal of Immunology* 162:1278-1286, 1999, describe CRTH2 receptor. Hirai, et al., *J. Exp. Med.* 193:255-261, 2001, indicates that CRTH2 is a receptor for $PGD_2$.

Th2-polarization has been seen in allergic diseases, such as asthma, allergic rhinitis, atopic dermatitis and allergic conjunctivitis (Romagnani S. Immunology Today, 18, 263-266, 1997; Hammad H. et al. Blood, 98, 1135-141 2001). Th2 cells regulate allergic diseases by producing Th2 cytokines, such as IL-4, IL-5 and IL-13 (Oriss et al., J. Immunol., 162, 1999-2007, 1999: Viola et al., Blood, 91, 2223-2230, 1998; Webb et al., J. Immunol., 165, 108-113, 200; Dumont F. J., Exp. Opin. Ther. Pat., 12, 341-367, 2002). These Th2 cytokines directly or indirectly induce migration, activation, priming and prolonged survival of effector cells, such as eosinophils and basophils, in allergic diseases (Sanz et al., J. Immunol., 160, 5637-5645, 1998 Pope et al., J. Allergy Clin. Immunol., 108, 594-601, 2001; Teran L. M., Clin. Exp. Allergy, 29, 287-290, 1999).

Therefore, antagonists which inhibit the binding of CRTH2 and $PGD_2$ should be useful for the treatment of allergic diseases, such as asthma, allergic rhinitis, atopic dermatitis and allergic conjunctivitis.

Ulven and Kostenis, *J. Med. Chem.*, 2005, 48(4):897-900 reports the synthesis of analogs of ramatroban that are selective potent CRTH2 antagonists. CRTH2 antagonists are also reported in patent applications: WO2003/097598, U.S. Pat. Nos. 7,220,760, 7,211,672, 7,166,607, US20070232681, US20070208004, US20070191416, US20070203209, US20070197587, US20070161698, US20070129355, US20060241109, US20060135591, US20060111426, US20060106081, US20060100425, US20060106061, US20050256158, US20060004030, US20050165033, US20050119268, EP147057, EP1556356, EP1784182, EP1833791, EP1814865, EP1828172, EP1761529, EP1758874, EP1756032, EP1718649, EP1675826, EP1633726, EP1556356, WO2006034419, WO2007062678, WO2007062677, WO2006111560, WO2007019675.

SUMMARY OF THE INVENTION

The present invention provides novel compounds which are CRTH2 receptor antagonists. Compounds of the present invention are useful for the treatment of various prostaglandin-mediated diseases and disorders; accordingly the present invention provides a method for the treatment of prostaglandin-mediated diseases using the novel compounds described herein, as well as pharmaceutical compositions containing them.

DETAILED DESCRIPTION OF THE INVENTION

The present invention relates to compounds of formula I:

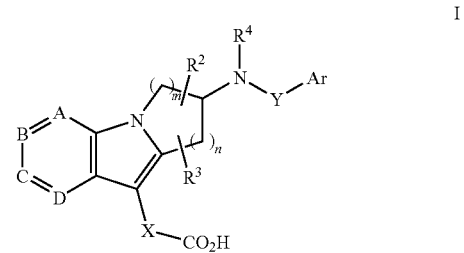

and pharmaceutically acceptable salts thereof, wherein:
one of A, B, C and D is N and the others are independently selected from N, CH and C($R^1$);
m is 1, 2, 3, or 4; preferably nm is 1 or 2;
n is 0, 1, 2, 3, or 4; preferably n is 1 or 2;
$R^1$ is a substituent group, as defined herein, or selected from H, halogen, $C_{1-6}$alkyl, $C_{1-6}$halogenated-alkyl, $OC_{1-6}$ halogenated-alkyl, $SC_{1-6}$ alkyl, $S(O)_tC_{1-6}$ alkyl, $S(O)_2NR^aR^b$, —$NR^aS(O)_2$alkyl, —$NR^aS(O)_2$aryl, CN, C(O) alkyl, C(O) aryl, C(O) heteroaryl, C(O)$NR^aR^b$, $NR^aC(O)$alkyl, $NR^aC(O)$aryl, aryl and heteroaryl. t is 0, 1 or 2. Multiple $R^1$ may represent different members of the group, i.e., one $R^1$ group may be halo and another $R^1$ group may be $C_{1-4}$ alkyl;
$R^2$, $R^3$ are a substituent group, as defined herein, or independently selected from the group consisting of: H, halo, $C_{1-4}$ alkyl, $C_{1-4}$ halogenated-alkyl, $C_{1-4}$ alkoxy, $C_{1-4}$ fluoroalkoxy and acetyl;
$R^4$ is selected from H, $C_{1-6}$ alkyl or halogenated $C_{1-6}$ alkyl;
Ar is aryl or heteroaryl each optionally substituted with a substituent group, as defined herein, or selected from H, halogen, $C_{1-6}$alkyl, $C_{1-6}$halogenated-alkyl, $OC_{1-6}$ halogenated-alkyl, $SC_{1-6}$ alkyl, $S(O)_tC_{1-6}$ alkyl, $S(O)_2NR^aR^b$, —$NR^aS(O)_2$alkyl, —$NR^aS(O)_2$aryl, CN, C(O) alkyl, C(O) aryl, C(O) heteroaryl, C(O)$NR^aR^b$, $NR^aC(O)$alkyl, $NR^aC(O)$aryl, aryl and heteroaryl. t is 0, 1 or 2;
X is selected from —C($R^a$)($R^b$)—, —C($R^aR^b$C($R^a$)($R^b$)—, C($R^a$)=C($R^a$)—, —OC($R^a$)($R^b$)—, and —SC($R^a$)($R^b$)—, —NHC($R^a$)($R^b$) or —$NR^2$C($R^a$)($R^b$);
Y is —S(O)$_2$- or —C(O)—;
$R^a$ and $R^b$ are independently H, halogen, aryl, heteroaryl, $C_{1-6}$ alkyl or halogenated $C_{1-6}$ alkyl; or
$R^a$ and $R^b$ together with the carbon atom to which they are both attached complete a $C_{3-6}$ cycloalkyl ring; or
$R^a$ and $R^b$ together with the adjacent carbon atoms to which they are attached complete a $C_{3-6}$ cycloalkyl ring.

In one subset of formula I are compounds wherein n is 1 or 2.

In another subset of formula I are compounds wherein m is 1 or 2.

In another subset of formula I are compounds wherein Ar is phenyl optionally substituted with 1 to 3 substituents independently selected from a substituent group, as defined herein, or selected from H, halogen, $C_{1-6}$alkyl, $C_{1-6}$halogenated-alkyl, $OC_{1-6}$ halogenated-alkyl, $SC_{1-6}$ alkyl, $S(O)_tC_{1-6}$ alkyl, $S(O)_2NR^aR^b$, —$NR^aS(O)_2$alkyl, —$NR^aS(O)_2$ aryl, CN, C(O) alkyl, C(O) aryl, C(O) heteroaryl, C(O)$NR^aR^b$, $NR^aC(O)$alkyl, $NR^aC(O)$aryl, aryl and heteroaryl. t is 0, 1 or 2. In one embodiment thereof Ar is phenyl substituted with 1 or 2 groups independently selected from halogen and $C_{1-6}$ alkoxy.

In another subset of formula I are compounds wherein X is —$C(R^a)(R^b)$—. In another embodiment of the invention, $R^a$ and $R^b$ may be independently selected from H, halogen, aryl, heteroaryl, $C_{1-6}$ alkyl, and halogenated $C_{1-6}$ alkyl. In another embodiment of the invention, $R^a$ and $R^b$ together with the carbon atom to which they are both attached complete a $C_{3-6}$ cycloalkyl ring. In yet another embodiment of the invention, $R^a$ and $R^b$ together with the adjacent carbon atoms to which they are respectively attached complete a $C_{3-6}$ cycloalkyl ring. In one embodiment of the invention X is methylene (—$CH_2$—). In another subset of compounds of the invention, X is —$SC(R^a)(R^b)$—.

According to another aspect of the invention, encompassed within compounds of formula I are compounds represented by formula IA,

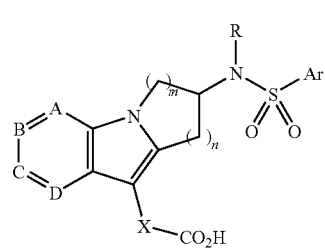

IA wherein one of A, B, C and D is N, and each of the others is independently selected from CH, and $C(R^1)$; R is H or $C_{1-3}$ alkyl; X is $CH_2$ or $SCH_2$; Ar is Ph or halogenated Ph; n is 1 or 2: and m is 1, and wherein $R^1$ is selected from $C_{1-3}$ alkyl, $C_{1-3}$ cycloalkyl, $C_{1-3}$ haloalkyl, and $SC_{1-3}$ alkyl.

In one subset of compounds of formula IA are those wherein $R^1$ is selected, for example, from Me, i-Pr, c-Pr, $CF_3$, and $SCH_3$. In another subset of compounds of formula IA are those wherein each of A, B, C and D is N or CH. According to two different aspects of the invention are: 1) those wherein a total of one of A, B, C, and D is N; and 2) those wherein a total of two of A, B, C, and D are N (see, for example, Table 1, infra).

A currently preferred subset of compounds of formula I may be represented by formula IIA.

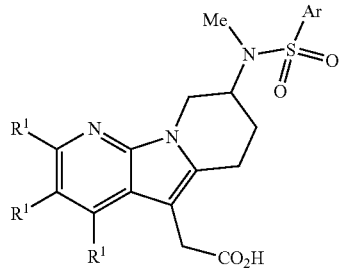

IIA for example, wherein n is 2, m is 1; X is $CH_2$; $R^2$ and $R^3$ are H: $R^4$ is Me; Ar is phenyl or substituted phenyl; A is N; B, C and D are —CH— or $C(R^1)$—; and $R^1$ is hydrogen, halogen, $C_{1-6}$ alkyl or $C_{1-6}$ halogenated alkyl.

Another subset of compounds of formula I may be represented by formula IIB,

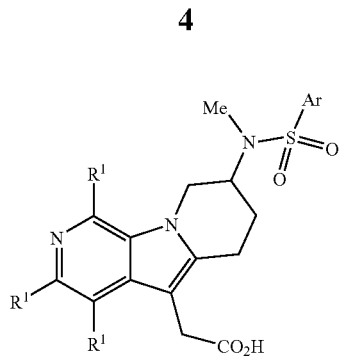

IIB for example, wherein n is 2, m is 1; X is $CH_2$, $R^2$ and $R^3$ are H; $R^4$ is Me; Ar is phenyl or substituted phenyl: B is N; A, C and D are —CH— or $C(R^1)$— and $R^1$ is hydrogen, halogen, $C_{1-6}$ alkyl or $C_{1-6}$ halogenated alkyl.

A further currently preferred subset of compounds of formula I may be represented by formula IIC,

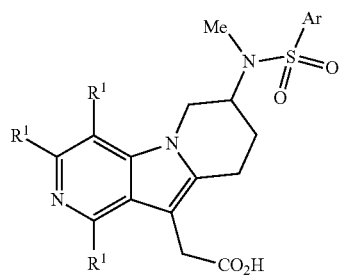

IIC for example, wherein n is 2, m is 1; X is $CH_2$; $R^2$ and $R^3$ are H; $R^4$ is Me; Ar is phenyl or substituted phenyl; C is N; A, B and D are —CH— or $C(R^1)$—; and $R^1$ is hydrogen, halogen, $C_{1-6}$ alkyl or $C_{1-6}$ halogenated alkyl.

A still further currently preferred subset of compounds of formula I may be represented by formula IID,

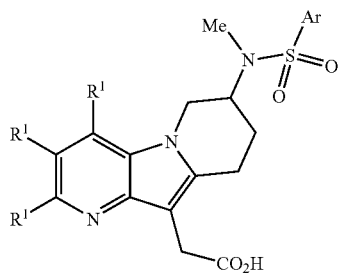

IID for example, wherein n is 2, m is 1; X is $CH_2$; $R^2$ and $R^3$ are H; $R^4$ is Me; Ar is phenyl or substituted phenyl; D is N; A, B and C are —CH— or $C(R^1)$—; and $R^1$ is hydrogen, halogen, $C_{1-6}$ alkyl and $C_{1-6}$ halogenated alkyl.

In a currently preferred embodiment of the invention, a compound of formula I may comprise a racemic mixture of {2-chloro-8-[(4-fluoro-benzenesulfonyl)-methyl-amino]-6,7,8,9-tetrahydro-pyrido[3,2-b]indolizin-5-yl}-acetic acid, or a pure form of either enantiomer.

In another currently preferred embodiment of the invention, a compound of formula I may comprise a racemic mixture of {8-[(4-fluoro-benzenesulfonyl)-methyl-amino]-6,7,8, 9-tetrahydro-pyrido[3,2-b]indolizin-5-yl}-acetic acid, or a pure form of either enantiomer.

The invention also encompasses pharmaceutical compositions containing a compound of formula I, and methods for treatment or prevention of prostaglandin mediated diseases using compounds of formula I.

Definitions:

The invention is described using the following definitions unless otherwise indicated.

The term "halogen" or "halo" includes F, C, Br, and I.

The term "alkyl" refers to linear or branched alkyl, chains containing the indicated number of carbon atoms. Non-limiting examples of alkyl groups include methylethyl, ethyl, propyl, isopropyl butyl, s- and t-butyl, pentyl, hexyl, heptyl, and the like.

"Halogenated-alkyl" means an alkyl group as described above wherein one or more hydrogen atoms have been replaced by halogen atoms, with up to complete substitution of all hydrogen atoms with halo groups. $C_{1-6}$ haloalkyl, for example, includes —$CF_3$, —$CF_2CF_3$ and the like.

"Alkoxy" means alkoxy groups of a straight, branched or cyclic configuration having the indicated number of carbon atoms. $C_{1-6}$ alkoxy, for example, includes methoxy, ethoxy, propoxy, isopropoxy, and the like.

"Halogenated-alkoxy" means an alkoxy group as described above in which one or more hydrogen atoms have been replaced by halogen atoms, with up to complete substitution of all hydrogen atoms with halo groups. $C_{1-6}$ haloalkoxy, for example, includes —$OCF_3$, —$OCF_2CF_3$ and the like.

"Aryl" means a 6-14 membered carbocyclic aromatic ring system comprising 1-3 benzene rings. If two or more aromatic rings are present, then the rings are fused together, so that adjacent rings share a common bond. Examples of aryl groups include phenyl and naphthyl.

The term "heteroaryl" (Het) as used herein means a 5-10 membered aromatic ring system containing one ring or two fused rings, and having 1-4 heteroatoms, selected from O, S and N. Het includes, but is not limited to, furanyl, diazinyl, imidazolyl, isooxazolyl, isothiazolyl, oxadiazolyl, oxazolyl, pyrazolyl, pyridyl, pyrrolyl, tetrazinyl, thiazolyl, thiadiazolyl, thienyl, triazinyl, triazolyl, 1H-pyrrole-2,5-dionyl, 2-pyrone, 4-pyrone, pyrrolopyridine, furopyridine and thienopyridine.

A "substituent group," as used herein, means a group selected from the following moieties:
(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, and heteroaryl, substituted with at least one substituent selected from:
  (i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "prophylaxis" means preventing or delaying the onset or the progression of a disease or disorder, or the signs and symptoms associated with such disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, with one or more pharmaceutically acceptable excipients.

For purposes of this specification, the following abbreviations have the indicated meanings Ac=acetyl; AcO=acetate; BOC=t-butyloxycarbonyl; CBZ=carbobenzoxy; CDI=carbonyldiimidazole; DCC=1,3-dicyclohexylcarbodiimide; DCE=1,2-dichloroethane; DIBAL=diisobutyl aluminum hydride; DIEA=N,N-diisoproylethylamine; DMAP=4-(dimethlylamino)pyridine; DMF=dimethylformamide; EDC=1-(3-dimethylaminopropyl)-3-ethylcarbodiimide HCl; ED-A=ethylenediaminetetraacetic acid, tetrasodium salt hydrate; FAB=fast atom bombardment; FMOC=9-fluorenylmethoxycarbonyl; HMPA=hexamethylphosphoramide; HATU=O-(7-azabenzotriazol-1-yl)N,N,N',N'-tetramethyluronium hexafluorophosphate; HOBt=1-hydroxybenzotriazole; HIRMS=high resolution mass spectrometry; ICBF=isobutyl chloroformate; KHIMDS=potassium hexamethyldisilazane; LDA=lithium diisopropylamide; MCPBA=metachloroperbenzoic acid; MMPP=magnesium monoperoxyphthlate hexahydrate; Ms=methanesulfonyl=mesyl; MsO=methanefulfonate=mesylate; NBS=N-bromosuccinimide; NMM=4-methylmorpholine; PCC=pyridinium chlorochromate; PDC=pyridinium dichromate; Ph=phenyl; PPTS=pyridinium p-toluene sulfonate; pTSA=p-toluene sulfonic acid; PyH.$Br_3$=pyridine hydrobromide perbromide; r.t.=room temperature; rac.=racemic; TFA=trifluoroacetic acid; TfO=trifluoromethanesulfonate=triflate; THF=tetraydrofuran; TLC=thin layer chromatography. Alkyl group abbreviations include: Me=methyl; Et=ethyl; n-Pr=normal propyl; i-Pr=isopropyl; c-Pr=cyclopropyl; n-Bu=normal butyl; i-Bu=isobutyl; c-Bu=cyclobutyl; s-Bu=secondary butyl; t-Bu=tertiary butyl.

Optical Isomers-Diastereomers-Geometric Isomers-Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I and formula IA.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Compounds of the formula I and formula IA may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general formula I or IA may be obtained by stereospecific synthesis using optically pure starting materials or reagents of known configuration.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I or IA are meant to also include the pharmaceutically acceptable salts.

Utilities and Therapeutic Use

The ability of compounds of formula I to interact with prostaglandin receptors makes them useful for preventing or reversing undesirable symptoms caused by prostaglandins in a mammalian, especially human subject. This mimicking or antagonism of the actions of prostaglandins indicates that the compounds of the invention and pharmaceutical compositions thereof are useful to treat, prevent, or ameliorate in mammals and especially in humans: respiratory conditions, allergic conditions, pain, inflammatory conditions, mucus secretion disorders, bone disorders, sleep disorders, fertility disorders, blood coagulation disorders, trouble of the vision as well as immune and autoimmune diseases. In addition, such a compound may inhibit cellular neoplastic transformations and metastic tumor growth and hence can be used in the treatment of various forms of cancer. Compounds of formula I may also be of use in the treatment and/or prevention prostaglandin-mediated proliferation disorders such as may occur in diabetic retinopathy and tumor angiogenesis. Compounds of formula I may also inhibit prostanoid-induced smooth muscle contraction by antagonizing contractile prostanoids or mimic king relaxing prostanoids and hence may be used in the treatment of dysmenorrhea, premature labor and eosinophil related disorders. More particularly compounds of formula I are antagonists of prostaglandin D2 receptor, CRTH2.

The invention in another aspect provides a method for antagonizing PGD2 receptors including CRTH2 receptor comprising administering to a mammal in need thereof an effective dose of a compound of formula I.

Another aspect of the invention provides a method of treating or preventing a prostaglandin mediated disease comprising administering to a mammalian patient in need of such treatment a compound of formula I in an amount which is effective for treating or preventing said prostaglandin mediated disease. Compounds and compositions of the invention may be used to treat prostaglandin mediated diseases including, but not limited to, allergic rhinitis, nasal congestion, rhinorrhea, perennial rhinitis, nasal inflammation, asthma including allergic asthma, chronic obstructive pulmonary diseases and other forms of lung inflammation; sleep disorders and sleep-wake cycle disorders; prostanoid-induced smooth muscle contraction associated with dysmenorrhea and premature labor; eosinophil related disorders; thrombosis; glaucoma and vision disorders; occlusive vascular diseases: congestive heart failure; diseases or conditions requiring a treatment of anti-coagulation such as post-injury or post surgery treatment; inflammation; gangrene; Raynaud's disease; mucus secretion disorders including cytoprotection; pain and migraine; diseases requiring control of bone formation and resorption such as for example osteoporosis; shock; thermal regulation including fever; and immune disorders or conditions in which immunoregulation is desirable. More particularly the disease to be treated is one mediated by prostaglandin D2 such as nasal congestion, pulmonary congestion, and asthma including allergic asthma.

In one embodiment of the invention is a method of treating or preventing a prostaglandin mediated disease comprising administering to a mammalian patient in need of such treatment a compound of formula I in an amount which is effective for treating or preventing a prostaglandin mediated disease, wherein the prostaglandin mediated disease is nasal congestion, rhinitis including allergic and perennial rhinitis, and asthma including allergic asthma.

In another embodiment of the present invention is a method of treating or preventing a prostaglandin D2-mediated disease comprising administering to a mammalian patient in need of such treatment a compound of formula I in an amount which is effective for treating or preventing a prostaglandin D2 mediated disease wherein said prostaglandin D2 mediated disease is nasal congestion or asthma.

In another embodiment of the present invention is a method for the treatment of nasal congestion in a patient in need of such treatment which comprises administering to said patient a therapeutically effective amount of a compound of formula I.

In yet another embodiment of the present invention is a method for the treatment of asthma, particularly allergic asthma, in a patient in need of such treatment which comprises administering to said patient a therapeutically effective amount of a compound of formula I.

Those skilled in the art will readily understand that for administration the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

A compound of formula I is administered orally or parenterally, e.g. by intravenous infusion (iv), intramuscular injection (im) or subcutaneously (sc).

Dose Ranges

The magnitude of a prophylactic or therapeutic dose of a compound of formula I will, of course, vary according to factors including the nature and the severity of a condition to be treated, the particular compound of formula I and its route of administration, etc. Effective dosages of compounds of formula I will also vary according to a variety of other factors including the age, weight, general health, sex, diet, time of administration, rate of excretion, drug combination and response of the individual patient. In general, the daily dose may be in the range of from about 0.001 mg to about 100 mg per kg body weight of a mammal, and preferably from about 0.01 mg to about 10 mg per kg. On the other hand, it may be necessary or preferred to use dosages outside these limits in some cases.

The amount of active ingredient that may be combined with the carrier materials to produce a single dosage form will vary depending upon the host treated and the particular mode of administration. For example, a formulation intended for oral administration to a human patient may contain from about 0.05 mg to about 5 g of active agent combined with an appropriate and convenient amount of carrier material wherein the amount of carrier material may vary from about 5 to about 99.95 percent of the total composition. Dosage unit forms will generally contain between from about 0.1 mg to about 0.4 g of a compound of formula I as active ingredient, typically 0.5 mg, 1 mg, 2 mg, 5 mg, 10 mg, 25 mg, 50 mg, 100 mg, 200 mg, or 400 mg.

Pharmaceutical Compositions

According to another aspect of the present invention there is provided pharmaceutical compositions comprising a compound of formula I with a pharmaceutically acceptable carrier. For the treatment of any of the prostanoid mediated diseases, e.g. as described herein, compounds of formula I may be administered orally, by inhalation spray, topically, parenterally or rectally in dosage unit formulations containing conventional non-toxic pharmaceutically acceptable carriers adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compounds of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any of the various methods known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets prepared according to the instant invention will contain an active ingredient of formula I in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for controlled release of the active ingredient.

Formulations of compounds of formula I for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions may contain the active material of formula I in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs containing a compound of the invention may be formulated with sweetening agents, for example glycerol, propylene glycol, sorbitol or sucrose. Such formulations may also contain a demulcent, a preservative and flavoring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. A pharmaceutical preparation according to the instant invention may also be in the form of a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used in addition, sterile, fixed oils are conventionally employed as a solvent or suspending medium. For this purpose any bland fixed oil may be employed including synthetic mono- or diglycerides. In addition, fatty acids such as oleic acid may find use in the preparation of injectables.

Compounds of formula I may also be administered in the form of suppositories for rectal administration of the active ingredient or drug. These compositions can be prepared by mixing the drug with a suitable non-irritating excipient which is solid at ambient temperatures but liquid at the rectal temperature and will therefore melt in the rectum to release the drug. Non-limiting examples of such excipients include cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, co-solvent, emulsifier, penetration enhancer, preservative system, and emollient. For the purposes of this patent application, the phrase "topical application" may include the use of mouth washes, gargles, and the like.

Actual methods of preparing such dosage forms are known, or will be apparent to the skilled in the art; See e.g. Remington's Pharmaceutical Sciences, Mack Publishing Co., Easton, Pa., 16$^{th}$ Ed., 1980.

Combinations with Other Drugs

For the treatment and prevention of prostaglandin mediated diseases, compound of formula I may be co-administered with other therapeutic agents. Thus in another aspect the present invention provides pharmaceutical compositions for treating prostaglandin mediated diseases comprising a therapeutically effective amount of a compound of formula I and one or more other therapeutic agents. Suitable therapeutic agents for combination therapy with a compound of formula I include: (1) a DP receptor antagonist such as S-5751 or laropiprant; (2) a corticosteroid such as triamcinolone acetonide; (3) a β-agonist such as salmeterol, formoterol, terbutaline, metaproterenol, albuterol and the like; (4) a leukotriene modifier, including a leukotriene receptor antagonist or a lipooxygenase inhibitor such as montelukast, zafirlukast, pranlukast, or zileuton; (5) an antibistamine such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (6) a decongestant including phenylephrine, phenylpropanolamine, pseudophedrine, oxymetazoline, ephinephrine, naphazoline, xylometazoline, propylhexedrine, or levo-desoxyephedrine; (7) an antiitussive including codeine, hydrocodone, caramiphen, carbetapentane, or dextramethorphan; (8) another prostaglandin ligand including prostaglandin F agonist such as latanoprost; misoprostol, enprostil, rioprostil, ornoprostol or rosaprostol; (9) a diuretic; (10) non-steroidal anti-inflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, nmefenanic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, rnofebutazone, oxyphenbutazonte, phenylbutazone); (11) cyclooxygenase-2 (COX-2) inhibitors such as celecoxib and rofecoxib; (12) inhibitors of phosphodiesterase type IV (PDE-IV) e.g. Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azatbioprine and 6-mercaptopurine, cytotoxic cancer chemotherapeutic agents, bradykinin (BK2) antagonists such as FK-3657, TP receptor antagonists such as seratrodast, neurokinin antagonists (NK1/NK2), VLA-4 antagonists such as those described in U.S. Pat. No. 5,510,332, WO97/03094, WO97/02289, WO96/40781, WO96/22966, WO9620216, WO96/01644, WO96/06108, WO95/15973 and WO96/31206.

In addition, the invention encompasses a method of treating prostaglandin $D_2$ mediated diseases comprising: administration to a patient in need of such treatment a non-toxic therapeutically effective amount of a compound of formula I, optionally co-administered with one or more of such ingredients as listed immediately above.

Preparation of Compounds

The compounds of this invention are made using well known chemical procedures. Compounds of Formula I of the present invention may be prepared, for example, according to the synthetic routes outlined in the following general schemes. If not commercially available, a necessary starting material for the preparation of a compound of formula I may be prepared by a procedure which is selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials.

Scheme 1

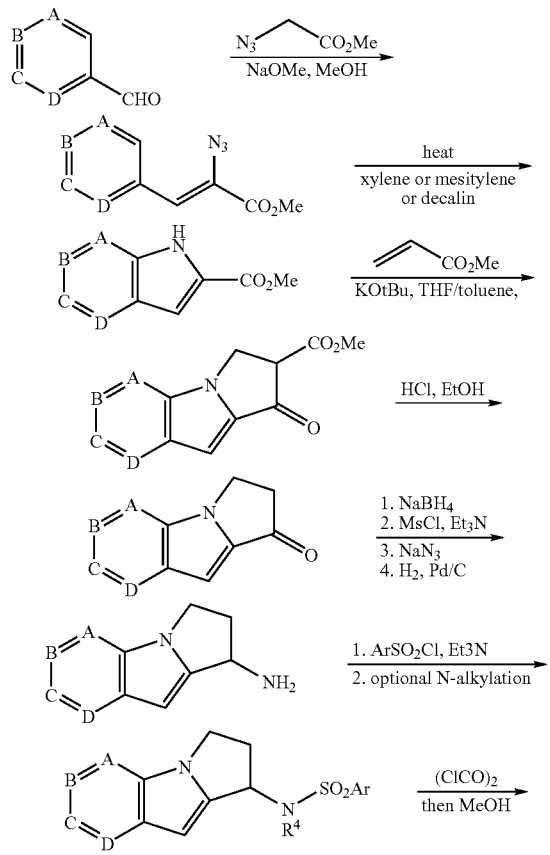

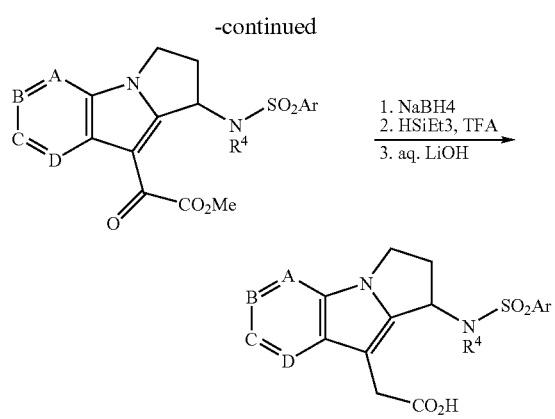

Scheme 2

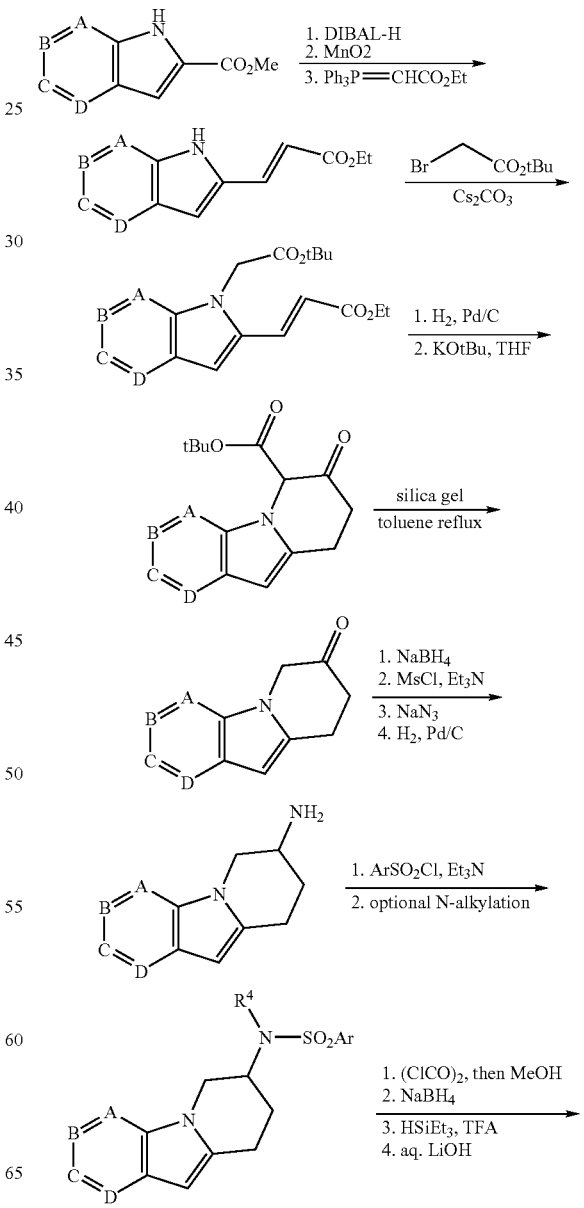

15
-continued
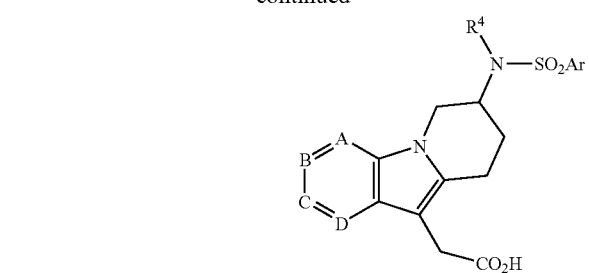
Scheme 3
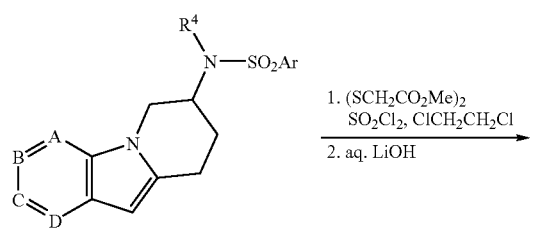
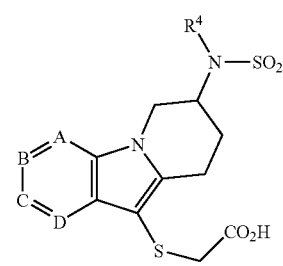
Scheme 4
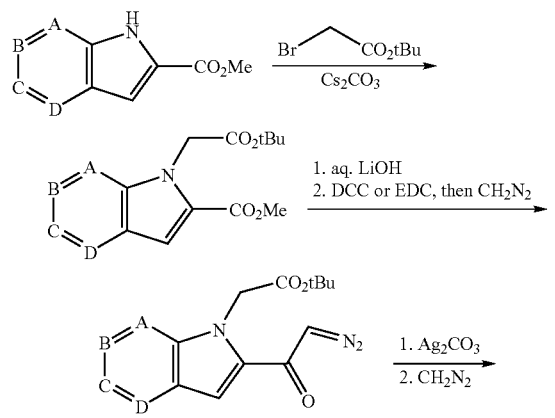
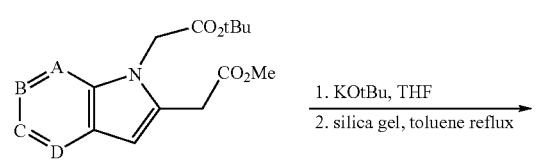
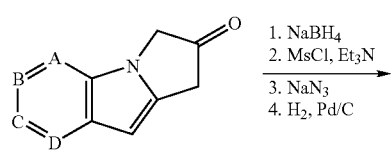
16
-continued
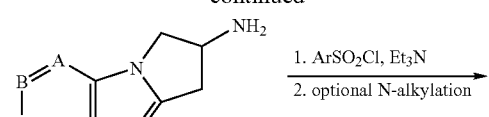
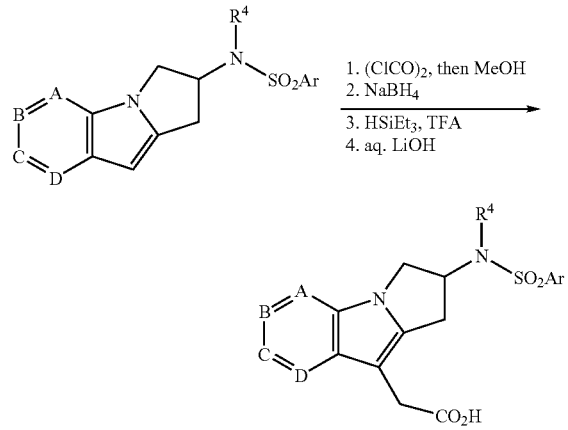
Scheme 5
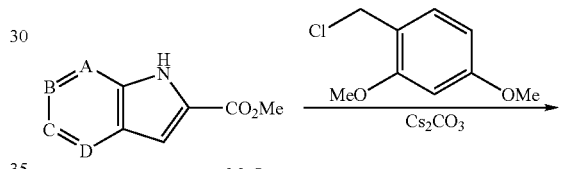
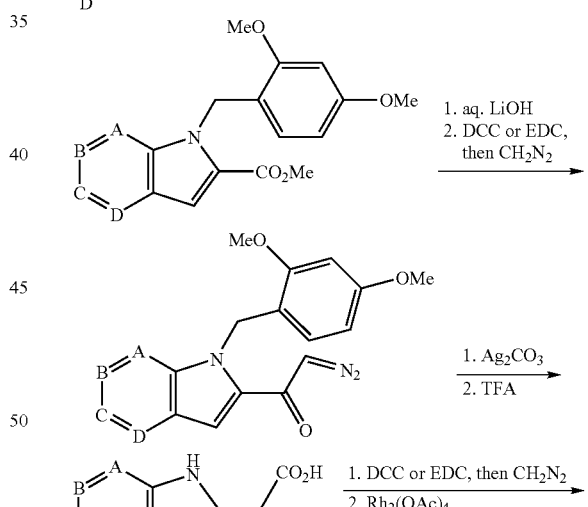
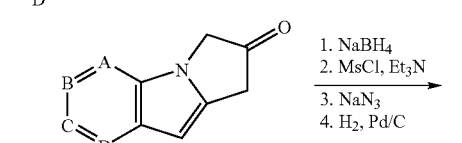
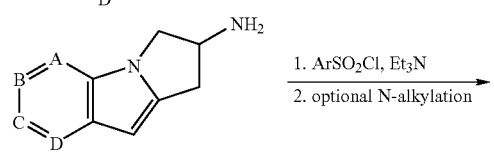

17
-continued
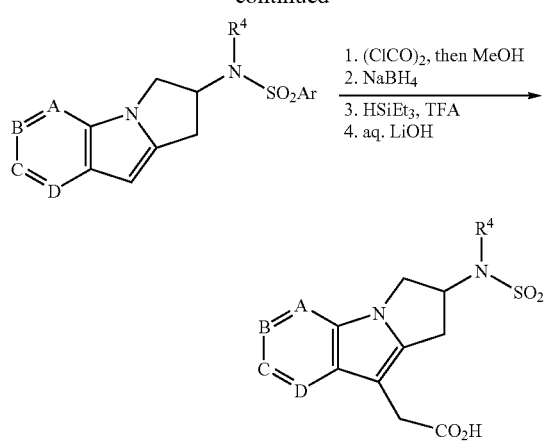
18
-continued
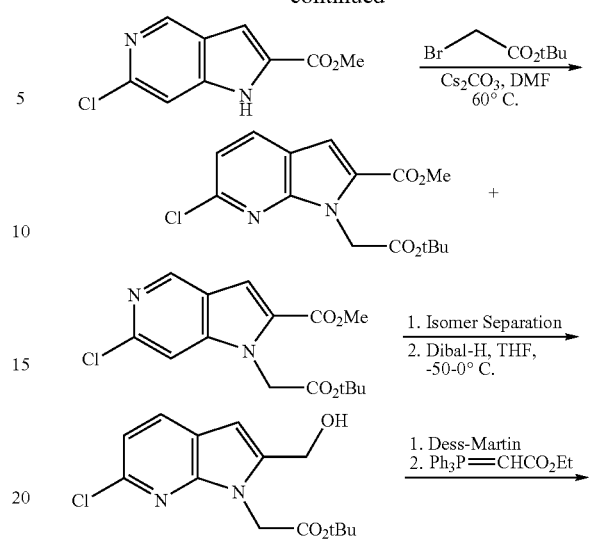
Scheme 6
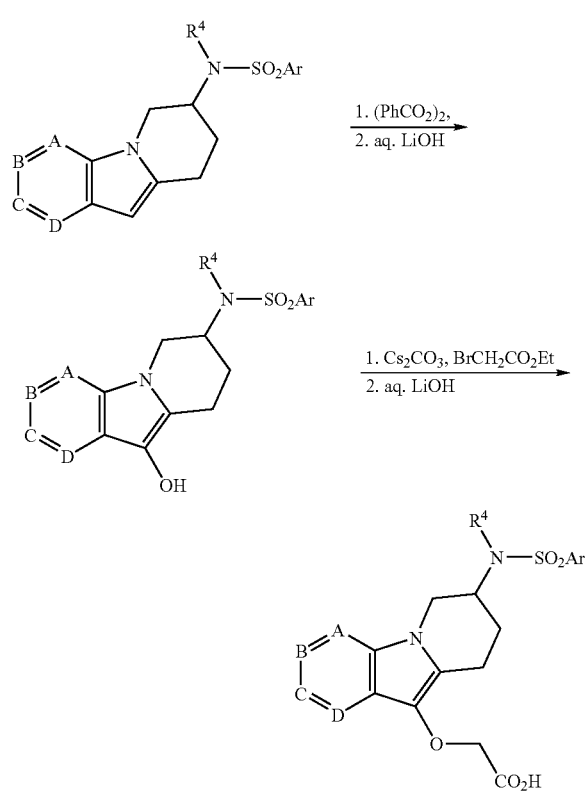
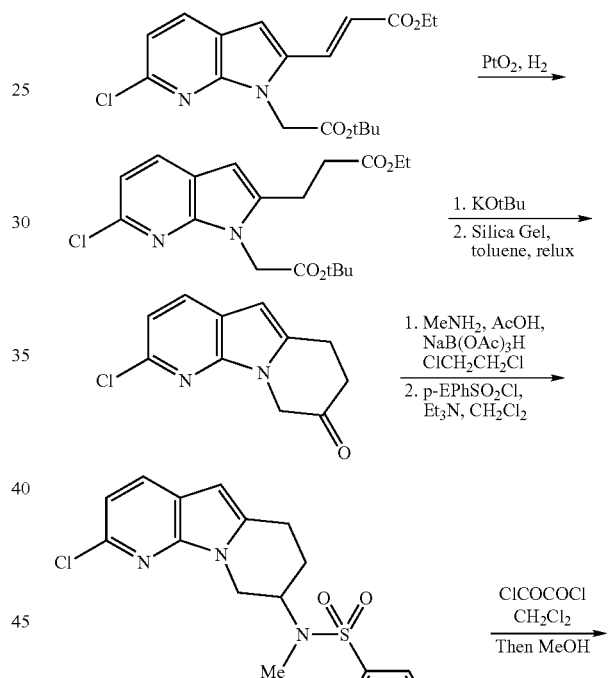
Scheme 7
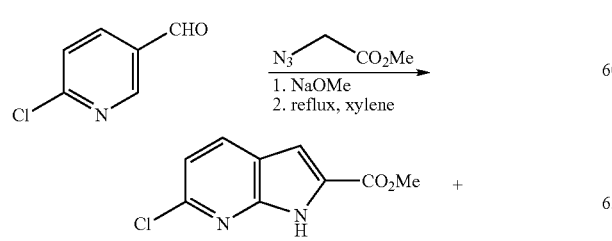
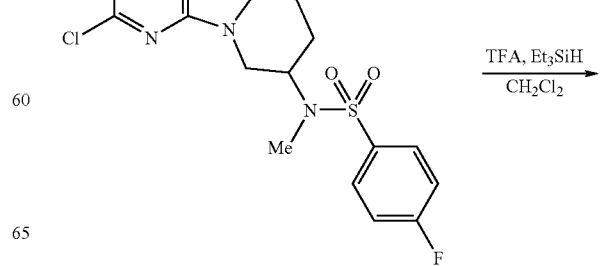

19

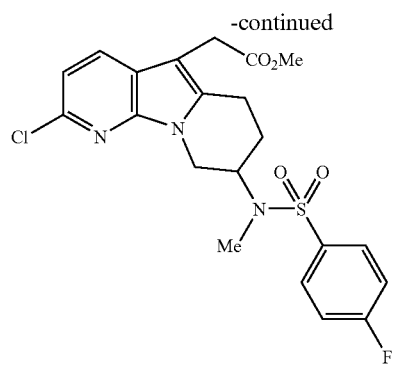

20

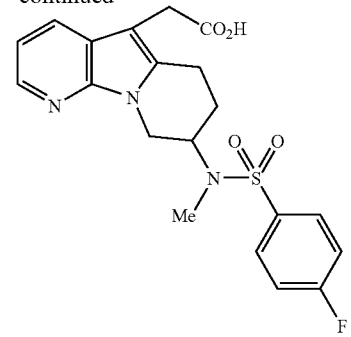

LiOH
Aq. THF

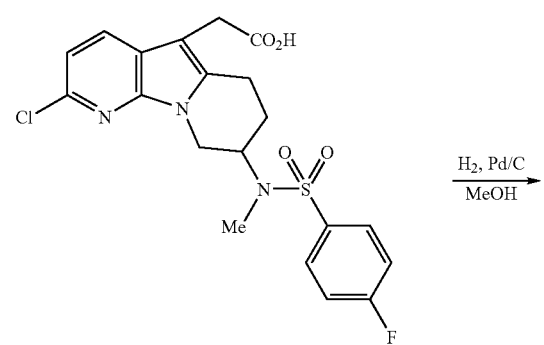

H₂, Pd/C
MeOH

Representative Compounds
Representative (but non-limiting) compounds of the invention are shown below in Table 1 with reference to formula IA:

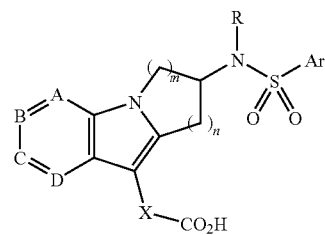

IA

TABLE 1

Some representative compounds of the invention.

| Cd | A | B | C | D | R | X | Ar | n | m |
|----|---|---|---|---|---|---|----|---|---|
| 1 | N | CH | CH | CH | CH₃ | CH₂ | Ph | 2 | 1 |
| 2 | N | CH | CH | CH | CH₃ | CH₂ | Ph | 1 | 1 |
| 3 | N | CH | CH | CH | H | SCH₂ | Ph | 2 | 1 |
| 4 | N | CH | CH | CH | CH₃ | SCH₂ | Ph | 1 | 1 |
| 5 | N | CH | CH | CH | H | CH₂ | 4-FPh | 2 | 1 |
| 6 | N | CH | CH | CH | CH₃ | CH₂ | 4-CF₃Ph | 1 | 1 |
| 7 | N | CH | CH | CH | CH₃ | SCH₂ | 4-ClPh | 2 | 1 |
| 8 | N | CH | CH | CH | CH₃ | SCH₂ | 3,4-diFPh | 1 | 1 |
| 9 | N | CCF₃ | CH | CH | CH₃ | CH₂ | Ph | 2 | 1 |
| 10 | N | CCH₃ | CH | CH | CH₃ | CH₂ | Ph | 2 | 1 |
| 11 | N | CH | CCH₃ | CH | CH₃ | CH₂ | 4-FPh | 2 | 1 |
| 12 | CH | N | CH | CH | CH₃ | CH₂ | Ph | 2 | 1 |
| 13 | CH | N | CH | N | CH₃ | CH₂ | Ph | 1 | 1 |
| 14 | CH | N | CH | CH | CH₃ | SCH₂ | 4-MeSO₂Ph | 2 | 1 |
| 15 | CH | N | CH | CH | CH₃ | SCH₂ | Ph | 1 | 1 |
| 16 | CH | N | CH | CH | H | CH₂ | 4-FPh | 2 | 1 |
| 17 | CH | N | CH | CH | CH₃ | CH₂ | 4-CF₃Ph | 1 | 1 |
| 18 | CH | N | CH | CH | CH₃ | SCH₂ | 4-ClPh | 2 | 1 |
| 19 | CH | N | CH | CH | CH₃ | SCH₂ | 3,4-diFPh | 1 | 1 |
| 20 | CH | N | CH | CH | CH₃ | CH₂ | Ph | 2 | 1 |
| 21 | Ci-Pr | N | CH | CH | CH₃ | CH₂ | Ph | 2 | 1 |
| 22 | N | CH | CH | N | CH₃ | CH₂ | Ph | 2 | 1 |
| 23 | CH | N | CH | CH | C₂H₅ | CH₂ | Ph | 2 | 1 |
| 24 | CH | N | CH | CH | CH₃ | CH₂ | Ph | 2 | 1 |
| 25 | N | CH | CH | CH | c-Pr | CH₂ | Ph | 2 | 1 |
| 26 | CH | CH | CCH₃ | N | CH₃ | CH₂ | Ph | 2 | 1 |
| 27 | CH | CH | C-iPr | N | CH₃ | CH₂ | Ph | 1 | 1 |
| 28 | CH | CH | C-cPr | N | CH₃ | SCH₂ | Ph | 2 | 1 |
| 29 | CH | N | CH | N | CH₃ | SCH₂ | Ph | 1 | 1 |
| 30 | CH | N | CCH₃ | N | CH₃ | CH₂ | 4-FPh | 2 | 1 |
| 31 | CH | CH | CSCH₃ | N | CH₃ | CH₂ | 4-CF₃Ph | 1 | 1 |
| 32 | CH | CH | CH | N | CH₃ | SCH₂ | 4-ClPh | 2 | 1 |
| 33 | CH | CH | CH | N | CH₃ | SCH₂ | 3,4-diFPh | 1 | 1 |
| 34 | CH | CCF₃ | CH | N | H | CH₂ | Ph | 2 | 1 |
| 35 | CH | CCH₃ | CH | N | CH₃ | CH₂ | Ph | 2 | 1 |

TABLE 1-continued

Some representative compounds of the invention.

| Cd | A | B | C | D | R | X | Ar | n | m |
|---|---|---|---|---|---|---|---|---|---|
| 36 | CH | CH | CH | N | $CH_3$ | $CH_2$ | Ph | 2 | 1 |
| 37 | CH | CH | CH | N | $CH_3$ | $CH_2$ | Ph | 1 | 1 |
| 38 | CH | CH | CH | N | $CH_3$ | $SCH_2$ | Ph | 2 | 1 |
| 39 | CH | CH | CH | N | $CH_3$ | $SCH_2$ | Ph | 1 | 1 |
| 40 | CH | CH | CH | N | $CH_3$ | $CH_2$ | 4-FPh | 2 | 1 |
| 41 | CH | CH | CH | N | $CH_3$ | $CH_2$ | 4-$CF_3$Ph | 1 | 1 |
| 42 | CH | CH | N | CH | $CH_3$ | $CH_2$ | Ph | 2 | 1 |
| 43 | CH | CH | N | C-iPr | H | $CH_2$ | Ph | 1 | 1 |
| 44 | CH | CH | N | CH | $CH_3$ | $SCH_2$ | Ph | 2 | 1 |
| 45 | CH | CH | N | CH | $CH_3$ | $SCH_2$ | Ph | 1 | 1 |
| 46 | CH | CH | N | CH | $CH_3$ | $CH_2$ | 4-FPh | 2 | 1 |
| 47 | CH | CH | N | CH | $CH_3$ | $CH_2$ | 4-$CF_3$Ph | 1 | 1 |
| 48 | CH | CH | N | CH | $CH_3$ | $SCH_2$ | 4-ClPh | 2 | 1 |
| 49 | CH | CH | N | CH | $CH_3$ | $SCH_2$ | 3,4-diFPh | 1 | 1 |
| 50 | CH | $CCF_3$ | N | CH | $CH_3$ | H | Ph | 2 | 1 |
| 51 | CH | $CCH_3$ | N | CH | $CH_3$ | $CH_2$ | Ph | 2 | 1 |
| 52 | CH | CH | N | CH | $CH_3$ | $CH_2$ | 3-thiophene | 2 | 1 |
| 53 | $CCH_3$ | CH | N | CH | H | $CH_2$ | Ph | 1 | 1 |
| 54 | CCl | CH | N | CH | $CH_3$ | $SCH_2$ | 2-thiophene | 2 | 1 |
| 55 | CF | CH | N | CH | $CH_3$ | $SCH_2$ | Ph | 1 | 1 |
| 56 | N | CH | N | CH | $CH_3$ | $CH_2$ | 4-pyridyl | 2 | 1 |
| 57 | N | CH | N | CH | $CH_3$ | $CH_2$ | 4-Cl-Ph | 1 | 1 |
| 58 | N | CH | N | CH | cPr | $CH_2$ | 3,4-diCl-Ph | 2 | 1 |
| 59 | N | CH | N | CH | iPr | $OCH_2$ | 4-Br-Ph | 2 | 1 |

Biological Assays

EXAMPLE B1

Radioligand Binding Assay

Radioligand binding assays are performed at room temperature in 10 mM HEPES/KOH pH 7.4, 1 mM EDTA containing 10 mM $MnCl_2$ and 0.4 nM [$^3$H]$PGD_2$ (NEN, 172 Ci $mmol^{-1}$), in a final volume of 0.2 ml. Competing ligands are diluted in dimethylsulfoxide ($Me_2SO$) kept constant at 1% (v/v) of the final incubation volume. The reaction is initiated by the addition of 23 μg of membrane protein prepared from a HEK-hCRTH2 cell line. Total and non-specific binding are determined in the absence and the presence of 10 μM $PGD_2$, respectively. Under these conditions, specific binding (total minus non-specific) of the radioligand to the receptor is expected to reach equilibrium within 50 min and is stable up to 180 min. The reaction is routinely conducted for 60 min at room temperature and terminated by rapid filtration through pre-wetted Unifilters GF/C (Packard), using a Tomtec MachIII semi-automated harvester (for HEK-hCRTH2). The filters are then washed with 4 ml of the same buffer and residual radioligand bound to the filter is determined by liquid scintillation counting following equilibration in 5 ml Ultima Gold™ (GF/C) or 50 μl Ultima Gold F™ (Unifilter) (Packard).

EXAMPLE B2

[cAMP] Measurements

HEK-hCRTH2 cells are grown to confluency on the day of the assay. The cells are washed with PBS, incubated for 3 min in cell dissociation buffer, harvested by centrifugation at 300 g for 6 min at room temperature and resuspended at $10^6$ cells $ml^{-1}$ in Hanks' balanced salt solution containing 25 mM HEPES pH 7.4 (HBSS/HEPES). The assay is performed in 0.2 ml HBSS/HEPES containing 100 000 cells, 5 μM forskolin (Sigma), 100 μM RO 20-1724 (Biomol) and the test compound at various concentrations. Following a 10 min pre-incubation of the cells with a test compound at 37° C. $PGD_2$ is added at a concentration of 3 μM to initiate the reaction. Following a 10 min incubation at 37° C., the reaction is stopped by a 3 min incubation in a boiling water bath. The samples are centrifuged for 10 min at 500 g and the cAMP content in the supernatant is determined using a [$^{125}$I]-cAMP scintillation proximity assay (Amersham). Maximal inhibition of forskolin stimulated cAMP production by activation of CRTH2 is determined in the presence of 1 μM $PGD_2$. All compounds are prepared in $Me_2SO$ kept constant at 1% (v/v) of the final incubation volume.

EXAMPLE B3

CRTH2 Binding Assay

The CRTH2 binding affinity of compounds of Formula I were assayed by MDS Pharma Service using the following reagents and conditions:
MDS Prostanoid CRTH2 Binding Assay (Catalog #268030):
Source: Human recombinant CHO-K1 cells
Ligand: 1 nM [$^3$H] Prostaglandin $D_2$ (PGD2)
Vehicle: 1% DMSO
Incubation Time/Temp: 2 hours @ 25° C.
Incubation Buffer: 50 mM Tris-HCl, pH 7.4, 40 mM $MgCl_2$, 0.1% BSA, 0.1% $NaN_3$
Non-Specific Ligand: 1 mM Prostaglandin $D_2$ ($PGD_2$)
$K_D$: 4.1 nM *
$B_{MAX}$: 13 pmole/mg Protein *
Specific Binding: 88% *
Quantitation Method Radioligand Binding
(* Historical Value)
See e.g. Sugimoto H, Shichijo M, Iino T, Manabe Y, Watanabe A, Shimazaki M, Gantner F and Bacon K B. (2003), "An orally bioavailable small molecule antagonist of CRTH2, ramatroban (BAY u3405), inhibits prostaglandin D2-induced eosinophil, migration in vitro", J Pharmacol Exp Ther. 305(1): 347-352

TABLE 2

| Inhibition of PGD$_2$ binding at 20 nM of tested compounds: | | |
|---|---|---|
| Example | Concentration | % inhibition |
| Example 2A | 20 nM | 97 |
| Example 2B | 20 nM | 0 |
| Example 4A | 20 nM | 91 |
| Example 4B | 20 nM | 0 |

The following synthetic examples are provided for illustrative purposes only and are not intended to limit the scope of the invention as defined in the claims.

EXAMPLE 1

(±)-{2-Chloro-8-[(4-fluoro-benzenesulfonyl)-methyl-amino]-6,7,8,9-tetrahydro-pyrido[3,2-b]indolizin-5-yl}-acetic acid

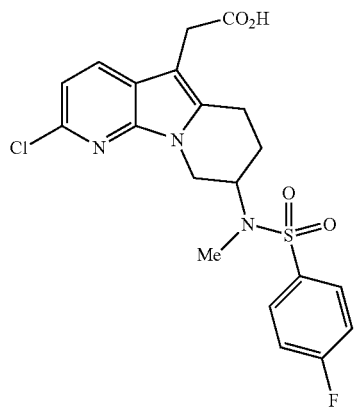 [SMILES: CN(C1CCc2c(CC(=O)O)c3ccc(Cl)nc3n2C1)S(=O)(=O)c1ccc(F)cc1]

Step 1 Azido-Acetic Acid Methyl Ester

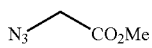

To a solution of 115 g of methyl bromoacetate in 1 L of methanol was added a solution of 71 g of sodium azide in 200 mL of water over 1 h at room temperature. The reaction was slightly exothermic and the reaction mixture was stirred for 3 h and methanol was removed under reduced pressure. The remaining aqueous mixture was extracted with 3×1 L of ether and the ether extract was dried over Na$_2$SO$_4$, filtered, and concentrated to give crude title compound which was used for the next step without further purification.

Step 2
6-chloro-1H-pyrrolo[2,3-b]pyridine-2-carboxylic acid methyl ester

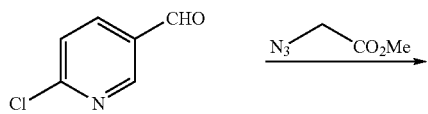

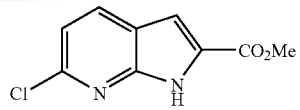

To a solution of NaOMe (35 nm, 4.37M in MeOH) and 70 mL of MeOH cooled at −20° C. was added a solution of 6-chloro-pyridine-3-carbaldehyde (10.9 g, 77 mmol) and azido-acetic acid methyl ester (22 g, 192.5 mmol) in 40 mL of MeOH dropwise over 10 min with a mechanical overhead stirrer. The resulting solution was stirred at 0° C. for 5 h and the cloudy mixture with light yellow solid was poured into 500 g of ice with stirring and the solid was collected by filtration, dried under vacuum to give 13 g of the intermediate. The intermediate was dissolved in 200 mL, of xylene and added dropwise over 20 main into 100 mL of boiling xylene. The mixture was refluxed for additional 4 h and concentrated. The residue was swished from 50 mL of 1:1 EtOAc/hexane to give 2.6 g of the desired product. NMR shows ~30% regioismeric indole (6-chloro-1H-pyrrolo[3,2-c]pyridine-2-carboxylic acid methyl ester) present.

6-Chloro-1H-pyrrolo[2,3-b]pyridine-2-carboxylic acid methyl ester $^1$H NMR (500 MHz, DMSO-d$_6$): δ 12.80 (1H, bs), 8.18 (1H, d), 7.23 (1H, d), 7.21 (1H, s), 3.88 (3H, s).

6-Chloro-1H-pyrrolo[3,2-c]pyridine-2-carboxylic acid methyl ester $^1$H NMR (500 MHz, DMSO-d$_6$): δ 12.53 (1H, bs), 8.80 (1H, s), 7.42 (1H, s), 7.35 (1H, s), 3.90 (3H, s).

Step 3 1-tert-butoxycarbonylmethyl-6-chloro-1H-pyrrolo[2,3-b]pyridine-2-carboxylic acid methyl ester

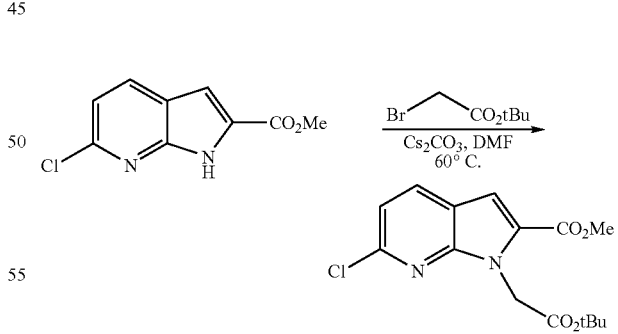

A mixture of 0.63 g of the product of Step 2 (containing ~30% of a regioisomer), 0.8 g of t-butyl bromoacetate and 1.5 g of Cs$_2$CO$_2$ in 15 mL of DMF was stirred at 60° C. for 2 h. The mixture was diluted with 30 mL of EtOAc, and filtered through a pad of silica gel. The filtrate was concentrated under reduced pressure and the residue was purified by silica gel chromatography eluted with 30% EtOAc/hexane to give 0.55 g of the desired product (fast eluting, white solid) along with 0.2 g of the isomer (slow eluting, white solid): 1-tert-butoxy-carbonylmethyl-6-chloro-1H-pyrrolo[3,2-c]pyridine-2-carboxylic acid methyl ester.

1-tert-Butoxycarbonylmethyl-6-chloro-1H-pyrrolo[2,3-b]pyridine-2-carboxylic acid methyl ester $^1$H NMR (500 MHz, acetone-$d_6$): δ 8.22 (1H, d), 7.38 (1H, s), 7.28 (1H, d), 5.30 (2H, s), 3.91 (3H, s), 1.46 (9H, s).

1-tert-Butoxycarbonylmethyl-6-chloro-1H-pyrrolo[3,2-c]pyridine-2-carboxylic acid methyl ester $^1$H NMR (500 MHz, acetone-$d_6$): δ 8.82 (1H, s), 7.73 (1H, s), 7.50 (1H, s), 5.34 (2H, s), 3.92 (3H, s), 1.44 (9H, s).

Step 4 (6-chloro-2-hydroxymethyl-pyrrolo[2,3-b]pyridin-1-yl)-acetic acid tert-butyl ester

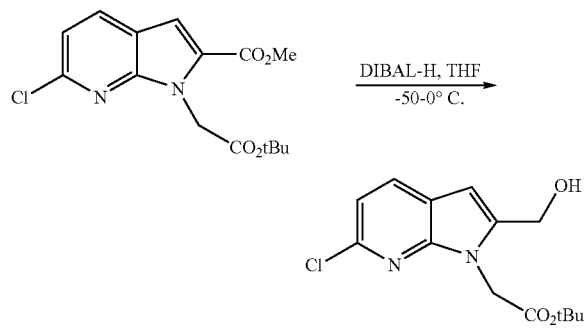

To a solution of 0.5 g of (6-chloro-2-hydroxymethyl-pyrrolo[2,3-b]pyridin-1-yl)-acetic acid tert-butyl ester in 10 mL of THF cooled at −50° C. was added dropwise 3.3 mL of 1.5 M diisobutylaluminum hydride solution in toluene. The reaction mixture was stirred between −50° C. and 0° C. for 2 h, and was then quenched by addition of 10 mL of 25% aqueous solution of K Na tartrate and 25 mL of EtOAc. After stirring for 1 h at room temperature, the organic layer was separated, dried over Na$_2$SO$_4$, concentrated. The residue was purified by silica gel chromatography eluted with 50% EtOAc/hexane to give 0.3 g of desired product as syrup.

$^1$H NMR (500 MHz, acetone-$d_6$): δ 7.95 (1H, d), 7.12 (1H, d), 6.48 (1H, s), 5.08 (2H, s), 4.77 (2H, bs), 4.42 (1, bs), 1.46 (9H, s).

Step 5 3-(1-tert-butoxycarbonylmethyl-6-chloro-1H-pyrrolo[2,3-b]pyridin-2-yl)-acrylic acid ethyl ester

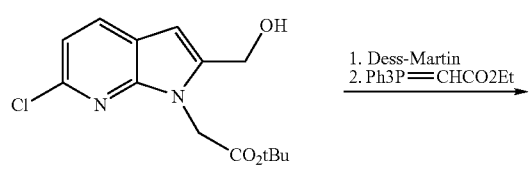

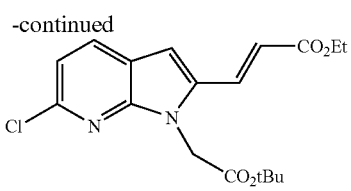

To a solution of 0.75 g of (6-chloro-2-hydroxymethyl-pyrrolo[2,3-b]pyridin-1-yl)-acetic acid tert-butyl ester in 50 mL of CH$_2$Cl$_2$ was added 1 g of Dess-Martin reagent. The mixture was stirred at room temperature for 30 min and diluted with 30 mL of CH$_2$Cl$_2$, filtered through a pad of silica gel. After concentration, the crude aldehyde intermediate was dissolved 40 mL of THF and treated with 1.2 g of Ph$_3$P=CHCO$_2$Et. The reaction mixture was stirred for 2 h at 55° C. and diluted with 30 mL of hexane, filtered through a pad of silica gel. The filtrate was concentrated and the residue was purified by silica gel chromatography eluted with 30%, EtOAc/hexane to give 0.9 g of title compound as a light yellow solid.

$^1$H NMR (500 MHz, acetone-$d_6$): δ 8.06 (1H, d), 7.70 (1H, d), 7.22 (1H, s), 7.21 (1H, d), 6.65 (1H, d), 5.23 (2H, s), 4.24 (2H, q), 1.49 (9H, s), 1.31 (3H, t).

Step 6 3-(1-tert-butoxycarbonylmethyl-6-chloro-1H-pyrrolo[2,3-b]pyridin-2-yl)-propionic acid ethyl ester

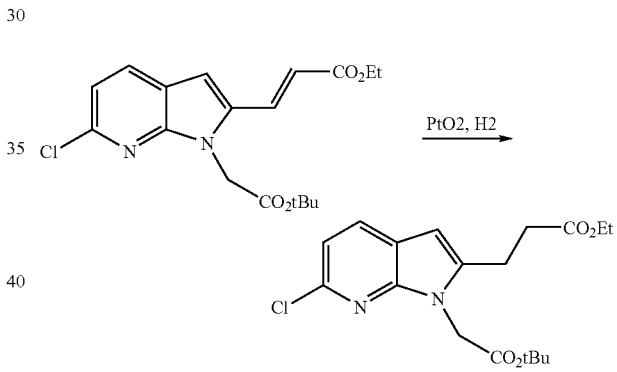

A mixture of 0.8 g of 3-(1-tert-butoxycarbonylmethyl-6-chloro-1H-pyrrolo[2,3-b]pyridin-2-yl)-acrylic acid ethyl ester and 80 mg of PtO$_2$ in 60 mL of EtOAc was stirred under a balloon pressure of H$_2$ for 1 h. The mixture was filtered through celite and concentrated to give crude product (0.8 g, white solid).

$^1$H NMR (500 M Hz, acetone-$d_6$): δ 7.90 (1H, d), 7.10 (1H, d), 6.36 (1H, s), 5.03 (2H, s), 4.13 (2H, q), 3.08 (2H, t), 2.80 (2H, t), 1.50 (9H, s), 1.22 (3H, t).

Step 7
2-chloro-6,7-dihydro-pyrido[3,2-b]indolizin-8-one

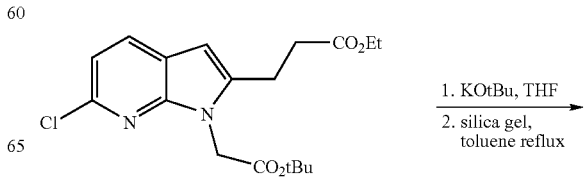

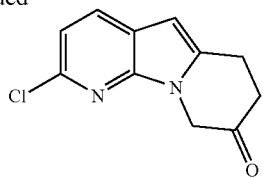

2.5 ml of 1M KOtBu THF solution was added to 20 mL of THF and the solution was cooled at −10° C. A solution of 3-(1-tert-butoxycarbonylmethyl-6-chloro-1H-pyrrolo[2,3-b]pyridin-2-yl)-propionic acid ethyl ester (0.73 g) in 4 mL of THF was added over 2 min. After stirring for 15 min at −10° C., 3 mL of 1 N HCL was added, followed by 10 mL brine. The mixture was extracted with 40 mL of EtOAc, dried over Na$_2$SO$_4$, filtered, and concentrated. The residue was dissolved in 30 mL of toluene and added 1 g of silica gel, and the resulting mixture was heated to reflux for 3 h. After cooling, the reaction mixture was filtered and concentrated. The residue was purified by silica gel chromatography eluted with 40% EtOAc/hexane to give 0.3 g of the title product as beige solid.

$^1$H NMR (500 MHz, acetone-d$_6$): δ 7.92 (1H, d), 7.10 (11, d), 6.48 (1H, s), 4.78 (2H, s), 3.34 (2H, q), 2.78 (2H, t).

Step 8 (±)-N-(2-chloro-6,7,8,9-tetrahydro-pyrido[3,2-b]indolizin-8-yl)-4-fluoro-N-methyl-benzenesulfonamide

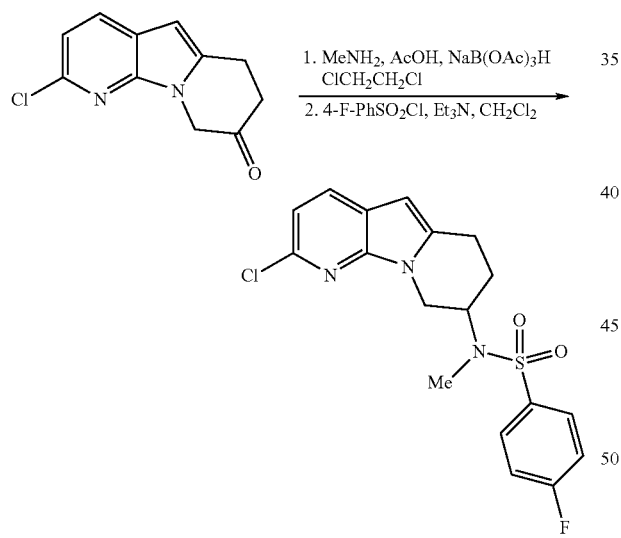

To a solution of 2-chloro-6,7-dihydro-pyrido[3,2-b]indolizin-8-one (0.3 g) in 8 mL of dichloroethane were added 1.5 mL of 2 M methylamine solution in THF, 0.18 mL of AcOH and 0.75 g of NaB(AcO)$_3$H. The mixture was stirred for 2 h at room temperature and was then treated with ~7 mL of 1N aqueous LiOH solution until slightly basic. The resulting mixture was extracted with 3×20 mL of CH$_2$Cl$_2$, dried over Na$_2$SO$_4$, filtered and concentrated. The residue was dissolved in 10 mL of CH$_2$Cl$_2$ and treated with 0.5 mL of Et$_3$N, 5 mg of DMAP and 0.3 g of 4-fluorobenzenesulfonyl chloride. The reaction mixture was stirred for 1 h at room temperature and then treated with 0.2 mL of water. After stirring for 10 min, the mixture was filtered through a pad of silica gel and concentrated. The residue was purified by silica gel chromatography eluted with 40% EtOAc/hexane to give 0.4 g of the title product as a white solid.

$^1$H NMR (500 MHz, acetone-d$_6$): δ 8.06 (2H, dd), 7.84 (11, d), 7.45 (2H, t), 7.08 (1H, d), 6.22 (H, s), 4.55 (1H, m), 4.32 (1H, dd), 3.92 (1H, t), 3.12 (1H, m), 3.05 (1H, m), 2.98 (3H, s), 2.03 (1H, m), 1.73 (1H, m).

Step 9 (±)-{2-chloro-8-[(4-fluoro-benzenesulfonyl)-methyl-amino]-6,7,8,9-tetrahydro-pyrido[3,2-b]indolizin-5-yl}-oxo-acetic acid methyl ester

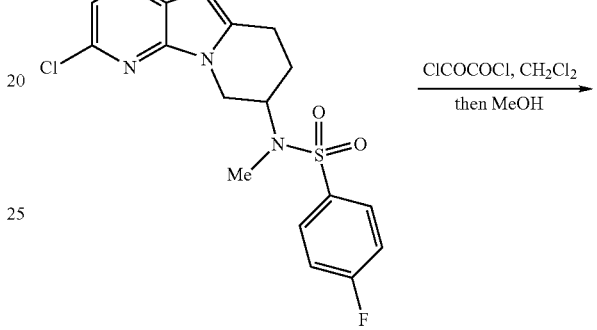

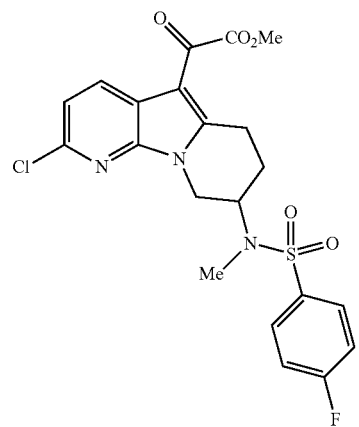

To a solution of (±)-N-(2-chloro-6,7,8,9-tetrahydro-pyrido[3,2-b]indolizin-8-yl)-4-fluoro-N-methyl-benzenesulfonamide (0.31 g) in 15 mL of CH$_2$Cl$_2$ cooled at 0° C. was added 0.15 mL of oxalyl chloride. After stirring for 30 min at 0° C., 6 mL of dry MeOH was added and stirring was continued for 20 min. The resulting solid was collected by filtration to give 0.28 g of the title compound as a white solid. (containing trace of MeOH).

$^1$H NMR (500 MHz, DMSO-d$_6$): δ 8.18 (2H, d), 8.01 (1H, dd), 7.50 (2H, t), 7.42 (1H, d), 4.55 (1H, m), 4.20 (1H, dd), 4.08 (1H, t), 3.95 (3H, s), 3.62 (1H, dd), 3.18 (1H, m), 2.83 (3H, s), 2.00 (1H, m), 1.62 (1H, m).

Step 10 (±)-{2-chloro-8-[(4-fluoro-benzenesulfonyl)-methyl-amino]-6,7,8,9-tetrahydro-pyrido[3,2-b]indolizi-5-yl}-acetic acid methyl ester

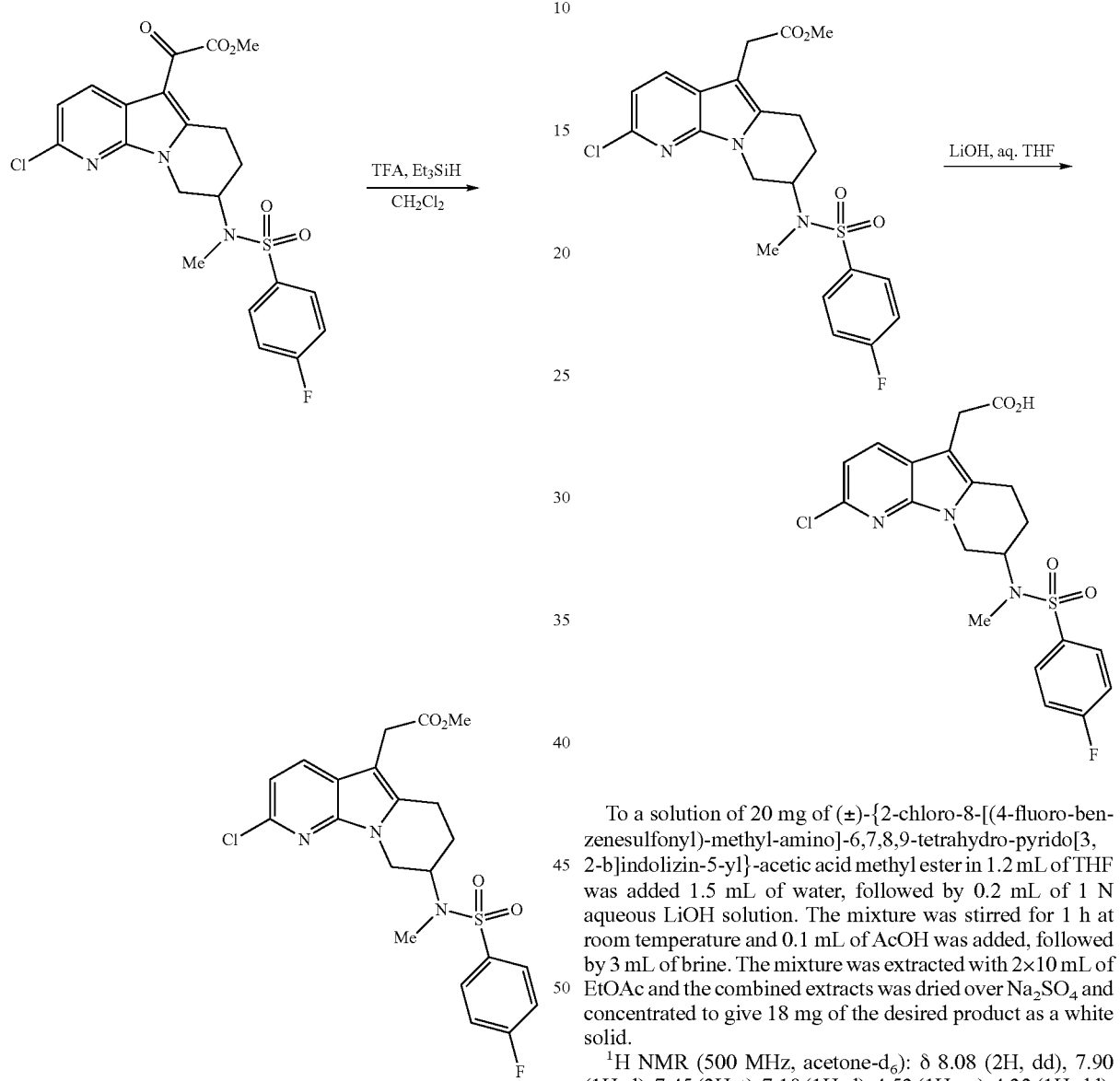

To a solution of (±)-{2 chloro-8-[(4-fluoro-benzenesulfonyl)-methyl-amino]6,7,8,9-tetrahydro-pyrido[3,2-b]indolizin-5-yl}-oxo-acetic acid methyl ester (0.26 g) in 4 mL of $Cl_2Cl_2$ were added 4 mL of trifluoroacetic acid and 4 mL of $Et_3SiH$. The reaction mixture was stirred overnight at room temperature and all volatile components were removed under vacuum. The residue was purified by silica gel chromatography eluted with 40% EtOAc/hexane to give 180 mg the title product as a white solid.

$^1$H NMR (500 MHz, acetone-$d_6$): δ 8.08 (2H, dd), 7.89 (1H, d), 7.45 (2H, t), 7.10 (1H, d), 4.52 (1H, m), 4.32 (1K, dd), 3.92 (1H, t), 3.72 (1, d, A of AB), 3.65 (1H, d, B of AB), 3.61 (3H, s) 3.17 (1H, dd), 2.98 (3H s), 2.92 (1H, m), 2.02 (1H, m), 1.79 (1H, m).

Step 11 (±)-{2-chloro-8-[(4-fluoro-benzenesulfonyl)-methyl-amino]-6,7,8,9-tetrahydro-pyrido[3,2-b]indolizin-5-yl}-acetic acid To a solution of 20 mg of (±)-{2-chloro-8-[(4-fluoro-benzenesulfonyl)-methyl-amino]-6,7,8,9-tetrahydro-pyrido[3,2-b]indolizin-5-yl}-acetic acid methyl ester in 1.2 mL of THF was added 1.5 mL of water, followed by 0.2 mL of 1 N aqueous LiOH solution. The mixture was stirred for 1 h at room temperature and 0.1 mL of AcOH was added, followed by 3 mL of brine. The mixture was extracted with 2×10 mL of EtOAc and the combined extracts was dried over $Na_2SO_4$ and concentrated to give 18 mg of the desired product as a white solid.

$^1$H NMR (500 MHz, acetone-$d_6$): δ 8.08 (2H, dd), 7.90 (1H, d), 7.45 (2H, t), 7.10 (1H, d), 4.53 (1H, m), 4.32 (1H, dd), 3.92 (1, t), 3.70 (l, d, A of AB), 3.62 (1H, d, B of AB), 3.20 (1H, dd), 3.00 (3H, s), 2.92 (1H, m), 2.02 (1H, m), 1.78 (1H, m).

EXAMPLE 2

HPLC chiral resolution of (±)-{2-chloro-8-[(4-fluoro-benzenesulfonyl)-methyl-amino]-6,7,8,9-tetrahydro-pyrido[3,2-b]indolizin-5-yl}-acetic acid (±)-{2-Chloro-8-[(4-fluorobenzenesulfonyl)-methyl-amino]-6,7,8,9-tetrahydro-pyrido[3,2-b]indolizin-5-yl}-acetic acid (EXAMPLE 1) was resolved on Chiralcel OJ-RH column (4.6×150 mm, Chiral Technologies, Cat. No. 17724, Lot No. OJRHCD-LL028) eluted with 0.05% TFA in Methanol. Two enantiomers were separated with retention time of 2.397 minute and 2.955 minute, respectively.

EXAMPLE 2A fast eluting enantiomeric 2-chloro-8-[(4-fluorobenzenesulfonyl)-methyl-amino]-6,7,8,9-tetrahydro-pyrido[3,2-b]indolizin-5-yl}-acetic acid

EXAMPLE 2B slow eluting enantimeric 2-chloro-8-[(4-fluorobenzenesulfonyl)-methyl-amino]-6,7,8,9-tetrahydro-pyrido[3,2-b]indolizi-5-yl}-acetic acid

EXAMPLE 3

(±)-{8-[(4-Fluoro-benzenesulfonyl-methyl-amino]-6,7,8,9-tetrahydro-pyrido[3,2-b]indolizin-5-yl}-acetic acid

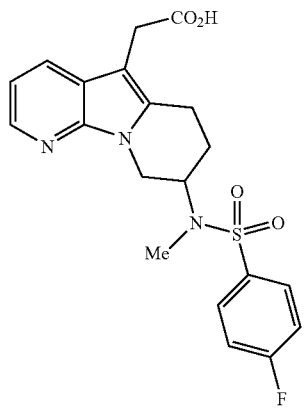

Step 1 (±)-{8-[(4-fluoro-benzenesulfonyl)-methyl-amino]-6,7,8,9-tetrahydro-pyrido[3,2-b]indolizin-5-yl}-acetic acid methyl ester

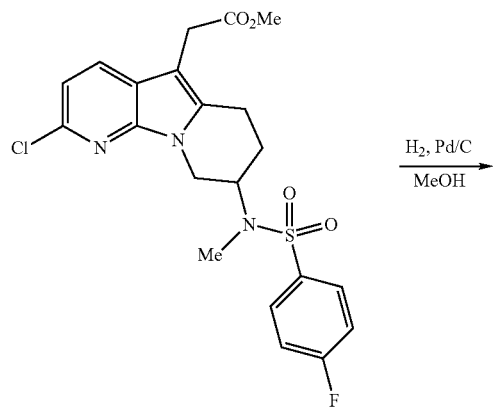

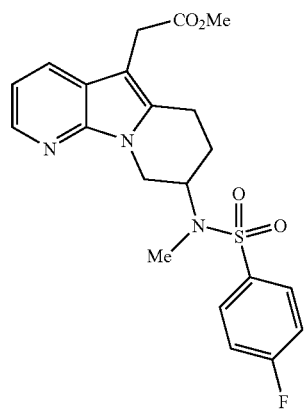 [SMILES: CN(C1CCc2c(CC(=O)O)c3cccnc3n2C1)S(=O)(=O)c1ccc(F)cc1]

A solution of the product of (±)-{2-chloro-8-[(4-fluoro-benzenesulfonyl)-methyl-amino]-6,7,8,9-tetrahydro-pyrido[3,2b]indolizin-5-yl}-acetic acid methyl ester (50 mg) and mg of Pd/C (20%) in 50 mL of MeOH was stirred under $H_2$ (balloon pressure) for 16 h. The suspension was filtered through celite and the filtrate was concentrated. The residue was purified by silica gel chromatography elated with 40% EtOAc/hexane to give 30 mg of the desired product as a white solid.

$^1$H NMR (500 MHz, acetone-$d_6$): δ 8.17 (1H, d), 8.10 (2H, dd), 7.85 (1H, d), 7.46 (2H, t) 7.05 (1H, dd), 4.53 (1H, m), 4.38 (1H, dd), 3.89 (1H, t) 3.70 (1H, d, A of AB), 3.64 (1H, d, B of AB), 3.62 (3H, s), 3.17 (1H, dd), 2.98 (3H, s), 2.92 (1H, m), 2.02 (1H, m), 1.78 (1H, m).

Step 2 (±)-{8-[(4-fluoro-benzenesulfonyl)-methyl-amino]-6,7,8,9-tetrahydro-pyrido[3,2-b]indolizin-5-yl}-acetic acid

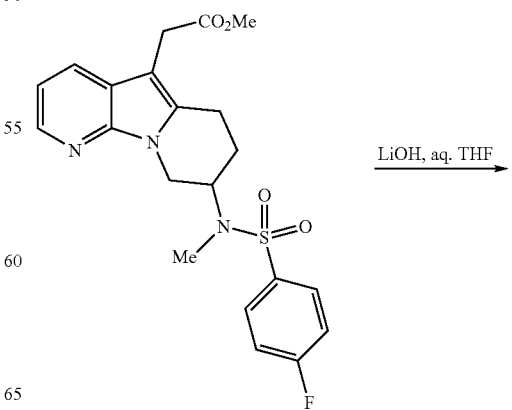

-continued

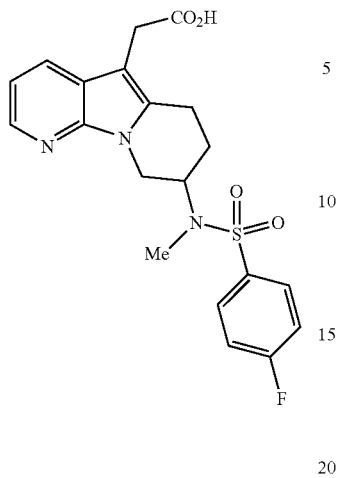

To a solution of (±)-{8-[(4-fluoro-benzenesulfonyl)-methyl-amino]6,7,8,9-tetrahydro-pyrido[3,2-b]indolizin-5-yl}-acetic acid methyl ester (28 mg) in 4 mL of 121 THF/water was added 0.2 mL of 1 N aqueous LiOH solution. After stirring for 1 h at room temperature, AcOH (0.2 mL) and 4 mL of brine were added and the mixture was extracted with 2×10 mL of EA, dried over $Na_2SO_4$. After filtration and concentration, the residue was purified by silica gel chromatography eluted with 50% EtOAc/hexane containing 5% AcOH to give 20 mg of the desired product as a white solid.

$^1$H NMR (500 MHz, acetone-de): δ 8.17 (1H, d), 8.10 (2H, dd), 7.88 (1H, d), 7.45 (2H, t), 7.05 (1H, dd), 4.53 (1H, m) 4.40 (1H, dd), 3.88 (1H, t), 3.67 (1H, d, A of AB), 3.60 (1H, d, B of AB), 3.18 (1H, dd), 2.98 (3H, s), 2.92 (1H, m), 2.01 (1H, m), 1.77 (1H, m).

EXAMPLE 4

HPLC chiral resolution of (±)-{8-[(4-fluoro-benzenesulfonyl)-methyl-amino]-6,7,8,9-tetrahydro-pyrido[3,2-b]indolizin-5-yl}-acetic acid (±)-{8-[(4-Fluoro-benzenesulfonyl)-methyl-amino]-6,7,8,9-tetrahydro-pyrido[3,2-b]indolizin-5-yl}-acetic acid (EXAMPLE 3) was resolved on Chiralcel OJ-RH column (4.6× 150 mm, Chiral Technologies, Cat. No. 17724, Lot No. OJRHCD-LL028) eluted with 0.05% TFA in Methanol. Two enantiomers were separated with retention time of 2.041 minute and 2.669 minute, respectively.

EXAMPLE 4A fast eluting enantiomeric 8-[(4-fluoro-benzenesulfonyl)-methyl-amino]-6,7,8,9-tetrahydro-pyrido[3,2-b]indolizin-5-yl}-acetic acid

EXAMPLE 4B slow eluting enantiomeric 8-[(4-fluoro-benzenesulfonyl)-methyl-amino]-6,7,8,9-tetrahydro-pyrido[3,2-b]indolizin-5-yl}-acetic acid

EXAMPLE 5

(±)-{3-Chloro-6-[(4-fluoro-benzenesulfonyl)-methyl-amino]-5,6,7,8-tetrahydro-2,4-b-diazafluoren-9-yl}-acetic acid

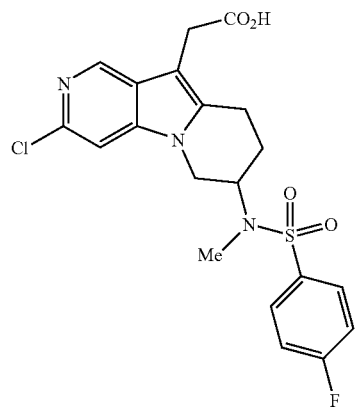 [SMILES: CN(C1CCc2c(CC(=O)O)c3cnc(Cl)cc3n2C1)S(=O)(=O)c1ccc(F)cc1]

Step 1 (6-chloro-2-hydroxymethyl-pyrrolo[3,2-c]pyridin-1-yl)-acetic acid tert-butyl ester

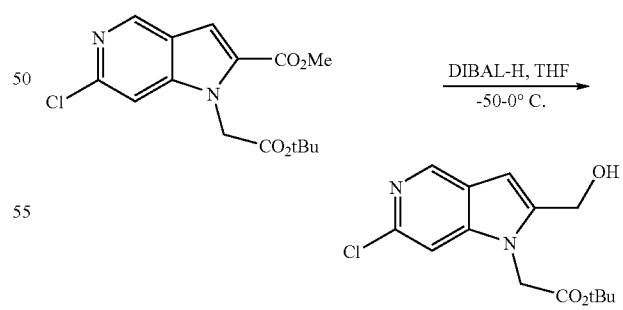

To a solution of 0.51 g of 1-tert-butoxycarbonylmethyl-6-chloro-1H-pyrrolo[3,2-c]pyridine-2-carboxylic acid methyl ester (the slower eluting product of Step 2 of EXAMPLE 1) in 15 mL of THF cooled at −50° C. was added dropwise 3.2 mL of 1.5 M DIBAL-H solution in toluene. The reaction mixture was stirred between −50° C. and 0° C. for 2 h, TLC showed ~80% conversion (60% EtOAc/H, Rf ~0.3) and the reaction was quenched by addition of 30 mL of 25% aqueous solution of K Na tartrate and 60 mL of EtOAc. After stirring for 1 h, the organic layer was separated, and the aqueous phase was extracted with 60 mL of more EtOAc, dried over $Na_2SO_4$, filtered, and concentrated. The residue was purified by silica gel chromatography eluted with 70% EtOAc/H to give 0.27 g of desired product as syrup.

Step 2 3-(1-tert-butoxycarbonylmethyl-6-chloro-1H-pyrrolo[3,2-c]pyridin-2-yl)-acrylic acid ethyl ester

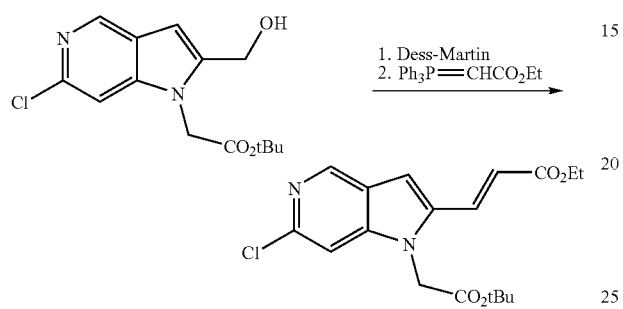

6-chloro-2-hydroxymethyl-pyrrolo[3,2-c]pyridin-1-yl)-acetic acid tert-butyl ester (0.075 g) was dissolved in 5 ml of $CH_2Cl_2$ and treated with 0.15 g of Dess-Martin reagent. The mixture was stirred at r.t. for 30 min and diluted with 10 mL of $CH_2Cl_2$, filtered through a pad of silica gel. After concentration, the residue was dissolved 10 mL of THF and treated with 0.3 g of $Ph_3P$=$CHCO_2Et$. The reaction mixture was stirred for 2 h at 55° C. and diluted with 10 mL of hexane, filtered through a pad of silica gel. The filtrate was concentrated and the residue was purified by silica gel chromatography eluted with 40% EtOAc/hexane to give 0.09 g of the title product as a light yellow solid. MS (ESI): 365.2 (M+1).

Step 3 3-(1-tert-Butoxycarbonylmethyl-6-chloro-1H-pyrrolo[3,2-c]pyridin-2-yl)-propionic acid ethyl ester

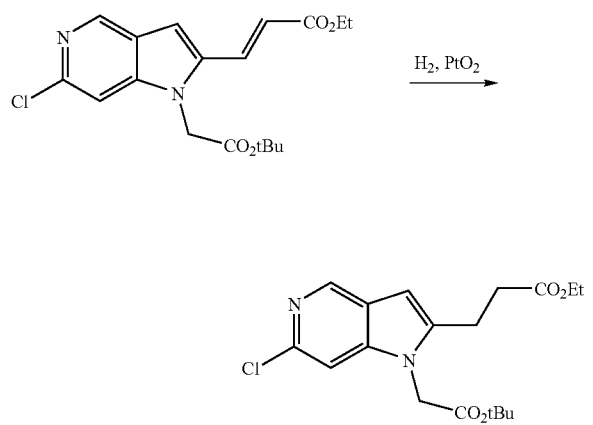 [SMILES: CCOC(=O)/C=C/c1cc2cnc(Cl)cc2n1CC(=O)OC(C)(C)C ; CCOC(=O)CCc1cc2cnc(Cl)cc2n1CC(=O)OC(C)(C)C]

A mixture of 0.08 g of 3-(1-tert-butoxycarbonylmethyl-6-chloro-1H-pyrrolo[3,2-c]pyridin-2-yl)acrylic acid ethyl ester and 0.015 g of $PtO_2$ in 12 mL of EtOAc was stirred under a balloon pressure of $H_2$ for 16 h. The mixture was filtered through celite and concentrated to give crude product (0.08 g, white solid) MS (ESI): 367.2 (M+1)

Step 4 3-chloro-7,8-dihydro-2,4-b-diaza-fluoren-6-one

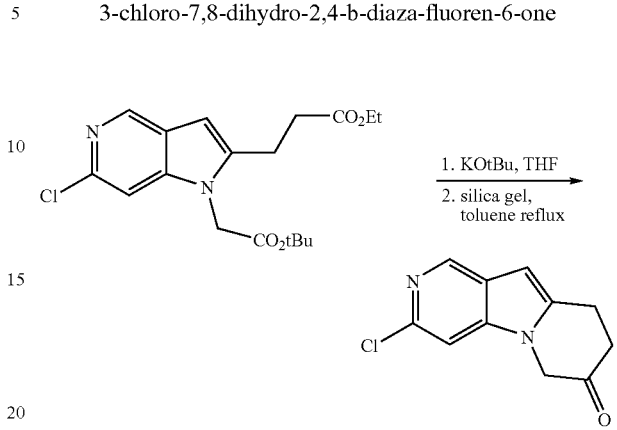

A solution of 0.25 ml of 1M KOtBu THF solution and 2 mL of THF was cooled at −10° C. A solution of 3-(1-tert-Butoxycarbonylmethyl-6-chloro-1H-pyrrolo[3,2-c]pyridin-2-yl)-propionic acid ethyl ester (0.07 g) in 0.5 mL of THF was added over r min. After stirring for 15 min at −10° C., 0.3 ml of 1 N HCl and 3 mL brine were added. The mixture was extracted with 10 mL of EtOAc, and extract was dried over $Na_2SO_4$, filtered, concentrated. The residue was dissolved in 10 mL of toluene and 0.3 g of silica gel was added, and the mixture was heated to reflux for 3 h. After cooling, the reaction mixture was filtered and concentrated. The residue was used for next step without further purification. MS (ESI): 221.1 (M+1).

Step 5 (±)-N-(3-chloro-5,6,7,8-tetrahydro-2,4b-diaza-fluoren-6-yl)-4-fluoro-N-methyl-benzene-sulfonamide

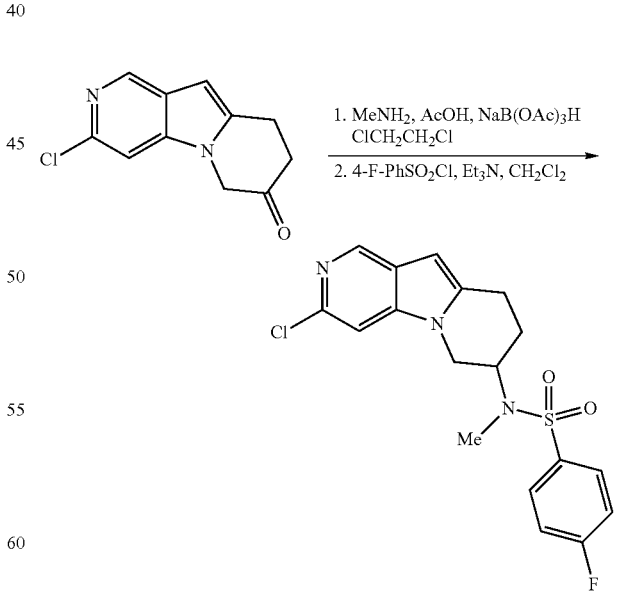

To a solution of 3-chloro-7,8-dihydro-2,4-b-diaza-fluoren-6-one (~0.055 g) in 4 mL of dichloroethane were added 0.2 mL of 2 M methylamine solution in THF, 0.02 mL of AcOH and 0.11 g of $NaB(AcO)_3H$. After stirring for 3 h at room temperature, the reaction mixture was treated with ~1 mL of 1N aqueous NaOH solution until slightly basic and was extracted with 3×7 mL of CH₂Cl₂, dried over Na₂SO₄, filtered and concentrated. The residue was dissolved in 2 mL of CH₂Cl₂ and treated with 0.1 mL of Et₃N, 1 mg of DMAP and 0.1 g of 4-fluorobenzenesulfonyl chloride. After stirring for 1 h at room temperature, 0.1 mL of water was added to the reaction mixture and after stirring for 30 min, the mixture was filtered through a pad of silica gel and concentrated. The residue was purified by silica gel chromatography eluted with 50% EtOAc/hexane to give 0.008 g of the title product as a white solid. MS (ESI): 394.1 (M+1).

Step 6 (±)-{3-chloro-6-[(4-fluoro-benzenesulfonyl)-methyl-amino]-5,6,7,8-tetrahydro-2,4b-diaza-fluoren-9-yl}-oxo-acetic acid methyl ester

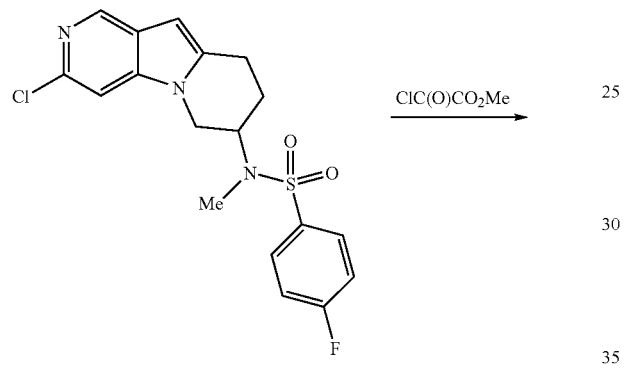

(±)-N-3-Chloro-5,6,7,8-tetrahydro-2,4b-diaza-fluoren-6-yl)-4-fluoro-N-methyl-benzenesulfonamide (0.008 g) was dissolved in 0.4 mL of ClCOCO₂Me and the solution was stirred for 3 days at 45° C. The reaction mixture was then concentrated under vacuum to give the 0.009 g of the title compound. MS (ESI): 480.1 (M+1).

Step 7 (±)-{3-chloro-6-[(4-fluoro-benzenesulfonyl)-methyl-amino]-5,6,7,8-tetrahydro-2,4b-diaza-fluoren-9-yl}-acetic acid methyl ester

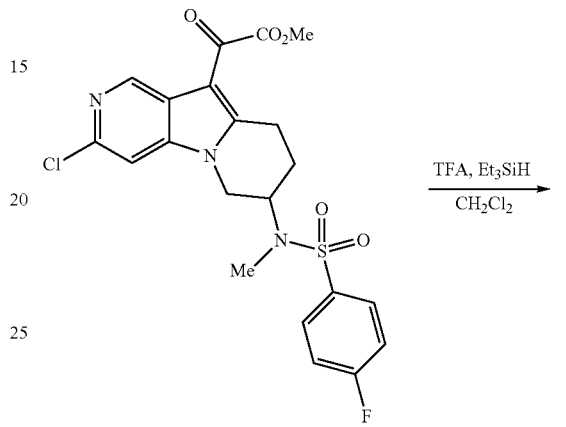

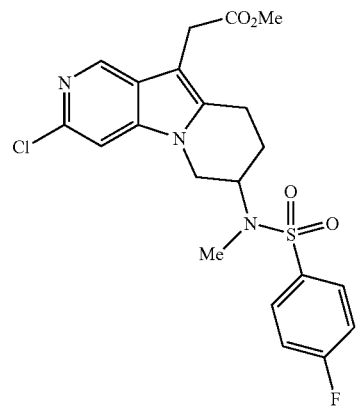

To a solution of (±)-{3-chloro-6-[(4-fluoro-benzenesulfonyl)-methyl-amino]-5,6,7,8-tetrahydro-2,4b-diaza-fluoren-9-yl}-oxo-acetic acid methyl ester (0.006 g) in 0.2 mL of CH₂Cl₂ were added 0.2 mL of TFA and 0.2 mL of Et₃SiH. The reaction mixture was stirred overnight at r.t. and concentrated under vacuum. The residue was purified by silica gel chromatography eluted with 50% EtOAc/hexane to give 0.005 g desired product as a white solid. MS (ESI): 466.1. (M+1).

Step 8 (±)-{3-chloro-6-[(4-fluoro-benzenesulfonyl)-methyl-amino]-5,6,7,8-tetrahydro-2,4b-diaza-fluoren-9-yl}-acetic acid

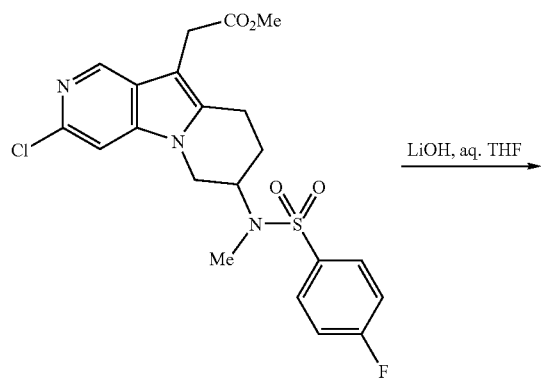

To a solution of 4 mg of (±)-{3-chloro-6-[(4-fluoro-benzenesulfonyl)-methyl-amino]-5,6,7,8-tetrahydro-2,4b-diaza-fluoren-9-yl}-acetic acid methyl ester in 0.2 mL of THF was added 0.1 mL of water, followed by 0.02 mL of 1 N aq. LiOH solution. After stirring for 1 h at room temperature, 0.05 mL of AcOH was added. The reaction mixture was the dried with a jet flow of nitrogen. The residue was suspended in 0.3 mL of EtOAc and filtered through silica gel. The filtrate was concentrated to give 2 mg of the title compound as a white solid. MS (ESI): 452.1 (M+1).

EXAMPLE 6

(±)-{8-[(4-Fluoro-benzenesulfonyl)-methyl-amino]-6,7,8,9-tetrahydro-pyrido[3,2-b]indolizin-5-yl}-acetic acid

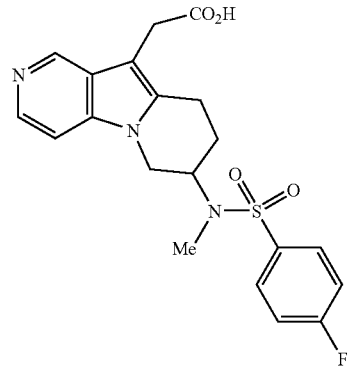

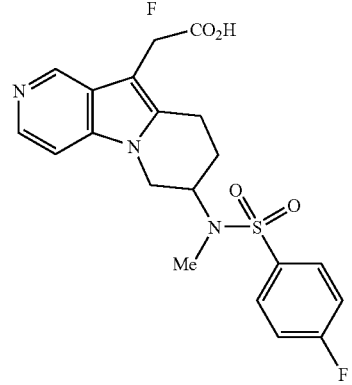

A solution of (±)-{3-chloro-6-[(4-fluoro-benzenesulfonyl)-methyl-amino]-5,6,7,8-tetrahydro-2,4b-diaza-fluoren-9-yl}-acetic acid (2 mg) and 2 mg of Pd/C (20%) in 0.5 mL of MeOH was stirred under Hz (balloon pressure) for 8 h. The suspension was filtered through celite and the filtrate was concentrated to give the title compound. MS (ES): 418.0 (M+1).

All patents, patent applications and publications cited in this application are hereby incorporated by reference in their entirety for all purposes to the same extent as if each individual patent, patent application or publication were so individually denoted.

It is to be understood that the foregoing relates to exemplary embodiments of the invention, and that the invention may find applications other than those described herein. None of the examples presented herein are to be construed as limiting the present invention in any way; variations and modifications may be made without departing from the spirit and scope of the invention as set forth in the following claims.

What is claimed is:

1. A compound of formula I:

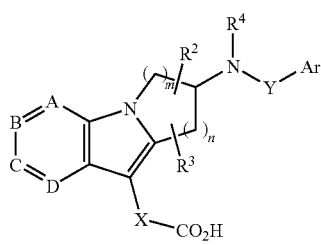

or a pharmaceutically acceptable salt thereof, wherein:
A is N and B, C, and D are independently selected from CH and C(R1);
m is an integer from 1 to 4;
n is an integer from 0 to 4;
$R^1$ is halogen;
$R^2$ and $R^3$ are hydrogen;
$R^4$ is selected from H, $C_{1-6}$ alkyl;
Ar is aryl optionally substituted with one or more halogen atoms;
X is —$C(R^a)(R^b)$—, wherein $R^a$ and $R^b$ are H;
Y is —$S(O)_2$—.

2. The compound, or salt thereof, of claim 1 wherein n and m are 1.

3. The compound or salt thereof of claim 1 wherein n is 2 and m is 1.

4. The compound or salt thereof of claim 1 wherein n is 2 and m is 1, $R^2$ and $R^3$ are H, and $R^4$ is methyl.

5. The compound or salt thereof of claim 1 wherein Ar is phenyl or substituted phenyl.

6. The compound or salt thereof of claim 1 wherein n is 2, m is 1, X is —$CH_2$—, $R^2$ and $R^3$ are H, $R^4$ is methyl, Ar is phenyl or substituted phenyl, and A is N.

7. The compound or salt thereof of claim 1 wherein n is 2, m is 1, X is —$CH_2$—, $R^2$ and $R^3$ are H, $R^4$ is Me, Ar is phenyl or substituted phenyl, and B is N.

8. The compound or salt thereof of claim 1 wherein n is 2, m is 1, X is —$CH_2$—, $R^2$ and $R^3$ are H, $R^4$ is methyl, Ar is phenyl or substituted phenyl, and C is N.

9. The compound or salt thereof of claim 1 wherein n is 2 and m is 1, X is —$CH_2$—, $R^2$ and $R^3$ are H, $R^4$ is methyl, Ar is phenyl or substituted phenyl, and D is N.

10. The compound of claim 1 comprising (±)-{2-chloro-8-[(4-fluoro-benzenesulfonyl)-methyl-amino]-6,7,8,9-tetrahydro-pyrido[3,2-b]indolizin-5-yl}-acetic acid.

11. The more active enantiomer of claim 10 which is the fast eluting on Chiralcel OJ-RH column when eluted with 0.05% TFA in Methanol.

12. The compound of claim 1 comprising (±)-{8-[(4-fluoro-benzenesulfonyl)-methyl-amino]-6,7,8,9-tetrahydro-pyrido[3,2-b]indolizin-5-yl}-acetic acid.

13. The more active enantiomer of claim 12 which is the fast eluting on Chiralcel OJ-RH column when eluted with 0.05% TFA in Methanol.

14. A pharmaceutical composition having the properties of CRTH2 receptor antagonists, comprising a pharmaceutically acceptable carrier, diluent, or excipient, and a compound of formula I or a pharmaceutically acceptable salt thereof according to claim 1.

15. A method of inhibiting PGD2 binding in a mammal by administering an inhibitory effective amount of a compound of Formula I or a pharmaceutically acceptable salt thereof according to claim 1.

* * * * *